US011191771B2

(12) United States Patent
Arthur et al.

(10) Patent No.: US 11,191,771 B2
(45) Date of Patent: Dec. 7, 2021

(54) COMBINATIONS OF PBD-BASED ANTIBODY DRUG CONJUGATES WITH FLT3 INHIBITORS

(71) Applicant: Seagen Inc., Bothell, WA (US)

(72) Inventors: William Arthur, Bainbridge Island, WA (US); Travis Biechele, Seattle, WA (US); Rory Rohm, Monroe, WA (US); Robert Thurman, Kenmore, WA (US)

(73) Assignee: Seagen Inc., Bothell, WA (US)

( * ) Notice: Subject to any disclaimer, the term of this patent is extended or adjusted under 35 U.S.C. 154(b) by 101 days.

(21) Appl. No.: 16/308,225

(22) PCT Filed: Jun. 8, 2017

(86) PCT No.: PCT/US2017/036605
§ 371 (c)(1),
(2) Date: Dec. 7, 2018

(87) PCT Pub. No.: WO2017/214433
PCT Pub. Date: Dec. 14, 2017

(65) Prior Publication Data
US 2019/0262354 A1   Aug. 29, 2019

Related U.S. Application Data

(60) Provisional application No. 62/347,758, filed on Jun. 9, 2016, provisional application No. 62/356,909, filed on Jun. 30, 2016, provisional application No. 62/490,334, filed on Apr. 26, 2017.

(51) Int. Cl.
| | | |
|---|---|---|
| *A61K 39/00* | (2006.01) | |
| *A61K 31/551* | (2006.01) | |
| *A61K 47/68* | (2017.01) | |
| *A61K 9/00* | (2006.01) | |
| *A61K 31/497* | (2006.01) | |
| *A61K 31/519* | (2006.01) | |
| *A61K 31/5377* | (2006.01) | |
| *A61K 31/553* | (2006.01) | |
| *A61K 31/706* | (2006.01) | |
| *C07K 16/28* | (2006.01) | |
| *A61K 31/4709* | (2006.01) | |
| *A61K 45/06* | (2006.01) | |

(52) U.S. Cl.
CPC .......... *A61K 31/551* (2013.01); *A61K 9/0019* (2013.01); *A61K 31/4709* (2013.01); *A61K 31/497* (2013.01); *A61K 31/519* (2013.01); *A61K 31/5377* (2013.01); *A61K 31/553* (2013.01); *A61K 31/706* (2013.01); *A61K 45/06* (2013.01); *A61K 47/6803* (2017.08); *A61K 47/6867* (2017.08); *C07K 16/28* (2013.01); *C07K 16/2866* (2013.01)

(58) Field of Classification Search
CPC .................. A61K 31/551; A61K 45/06; A61K 47/6867; A61K 47/6803; C07K 16/28; A61P 35/00
See application file for complete search history.

(56) References Cited

U.S. PATENT DOCUMENTS

| | | |
|---|---|---|
| 7,419,811 B2 | 9/2008 | Lavie et al. |
| 7,695,716 B2 | 4/2010 | Drachman et al. |
| 8,337,855 B2 | 12/2012 | Hoffee et al. |
| 8,455,622 B2 | 6/2013 | McDonagh et al. |
| 9,061,074 B2 | 6/2015 | Carter et al. |
| 9,079,958 B2 | 7/2015 | Konopitzkly et al. |
| 9,352,006 B2 | 5/2016 | Chen |
| 9,550,833 B2 | 1/2017 | Konopitzky et al. |
| 9,587,019 B2 | 3/2017 | Sutherland et al. |
| 2002/0022031 A1 | 2/2002 | Goldenberg et al. |
| 2004/0152632 A1 | 8/2004 | Feingold |
| 2007/0190060 A1 | 8/2007 | Boghaert et al. |
| 2008/0104734 A1 | 5/2008 | Kav et al. |
| 2010/0158909 A1 | 6/2010 | McDonagh et al. |
| 2010/0278779 A1 | 11/2010 | Zeldis |
| 2011/0206700 A1 | 8/2011 | Hoffee et al. |
| 2011/0300139 A1 | 12/2011 | Kumar et al. |
| 2012/0082670 A1 | 4/2012 | Konopitzky et al. |
| 2012/0251554 A1 | 10/2012 | Bachmann et al. |
| 2013/0004432 A1* | 1/2013 | Pierres ............... C07K 16/2827 424/9.34 |
| 2013/0024177 A1 | 1/2013 | Nolan |
| 2013/0028919 A1 | 1/2013 | Howard et al. |
| 2013/0058919 A1 | 3/2013 | Lazar et al. |
| 2013/0109644 A1 | 5/2013 | MacBeth et al. |
| 2013/0309223 A1 | 11/2013 | Sutherland et al. |
| 2014/0011215 A1 | 1/2014 | Albitar et al. |
| 2014/0086942 A1 | 3/2014 | Carter et al. |
| 2014/0335549 A1 | 11/2014 | Albitar et al. |

(Continued)

FOREIGN PATENT DOCUMENTS

| | | |
|---|---|---|
| CA | 2733223 A1 | 2/2010 |
| EP | 2625201 B1 | 9/2016 |

(Continued)

OTHER PUBLICATIONS

Zarrinkar et al Blood, vol. 114(14) p. 2984 (2009) (Year: 2009).*
Almagro, et al., "Humanization of antibodies", Frontiers in Bioscience 13, pp. 1619-1633, (Jan. 1, 2008).
Author Unknown, "History of Changes for Study: NCT02785900 Vadastuximab Talirine (SGN-CD33A; 33A) Combined With Azacitidine or Decitabine in Older Patients With Newly Diagnosed Acute Myeloid Leukemia (CASCADE)", ClinicalTrials.Gov, Available at: https://clinicaltrials.gov/ct2/history/CT02785900?V_2=View#StudyPageTop, 8 pages, (Accessed Jun. 2019).
Balaian, et al., "5-Azacytidine Augments the Cytotoxicity of Mylotarg toward AML Blasts in Vitro and in Vivo", Blood, 110(11), 1835, (Nov. 2007).

(Continued)

*Primary Examiner* — Sheela J. Huff
(74) *Attorney, Agent, or Firm* — Seagen Inc.

(57) ABSTRACT

This invention relates to treatment of cancer using a antibody drug conjugates that comprise PBD molecules in combination with FLT3 inhibitors.

8 Claims, 12 Drawing Sheets

Specification includes a Sequence Listing.

(56) References Cited

U.S. PATENT DOCUMENTS

| | | | |
|---|---|---|---|
| 2015/0125447 A1 | 5/2015 | Heider | |
| 2016/0068601 A1 | 3/2016 | Brogdon et al. | |
| 2016/0095863 A1* | 4/2016 | Taube | A61K 31/5377 |
| | | | 514/233.2 |
| 2016/0096892 A1 | 4/2016 | Brogdon et al. | |
| 2017/0204180 A1 | 7/2017 | Sutherland et al. | |
| 2019/0076549 A1 | 3/2019 | Arthur et al. | |
| 2019/0117787 A1 | 4/2019 | Kennedy et al. | |
| 2019/0134215 A1 | 5/2019 | Kennedy et al. | |

FOREIGN PATENT DOCUMENTS

| | | | |
|---|---|---|---|
| WO | WO2004/043344 A2 | 5/2004 | |
| WO | WO2004/043461 A1 | 5/2004 | |
| WO | WO2008/070593 A2 | 6/2008 | |
| WO | WO2008/070593 A3 | 6/2008 | |
| WO | WO2011/106389 A1 | 9/2011 | |
| WO | WO2011/130613 A1 | 10/2011 | |
| WO | WO2012/045752 A1 | 4/2012 | |
| WO | WO2013/173496 A2 | 11/2013 | |
| WO | WO2014/165119 A1 | 10/2014 | |
| WO | WO2015/067570 A2 | 5/2015 | |
| WO | WO2015/067570 A3 | 5/2015 | |
| WO | WO2015/179400 A2 | 11/2015 | |
| WO | WO-2016201065 A1 * | 12/2016 | A61P 35/00 |
| WO | WO2017/160954 A1 | 9/2017 | |
| WO | WO2017/180768 A1 | 10/2017 | |
| WO | WO2017/210621 A1 | 12/2017 | |
| WO | WO2017/214433 A1 | 12/2017 | |

OTHER PUBLICATIONS

Barthelemy, et al., "Comprehensive Analysis of the Factors Contributing to the Stability and Solubility of Autonomous Human $V_H$ Domains", The Journal of Biological Chemistry, vol. 283, No. 6, pp. 3639-3654, (Feb. 8, 2008).

Beiboer, et al., "Guided Selection of a Pan Carcinoma Specific Antibody Reveals Similar Binding Characteristics yet Structural Divergence Between the Original Murine Antibody and its Human Equivalent", J. Mol. Biol. 296, pp. 833-849, (2000).

Biddle-Snead, et al., "Assessment of myeloblast CD33 receptor occupancy (RO) by vadastuximab talirine in patients with acute myeloid leukemia (AML) receiving monotherapy treatment", Cancer Research. Proceedings: AACR Annual Meeting 2017, 77(13 supplement), Abstract CT120, (2017).

Bixby, et al., "Vadastuximab Talirine Monotherapy in Older Patients with Treatment Naive CD33-Positive Acute Myeloid Leukemia (AML)", Blood, 128(22):590, (2016).

Brown et al., "Combinations of the FLT3 inhibitor CEP-701 and chemotherapy synergistically kill infant and childhood MLL-rearranged ALL cells in a sequence-dependent manner" Leukemia 20, 1368-1376, (2006).

Brunetti et al., "CD123 (IL-3Ra) Is Consistently Expressed on Acute Myeloid Leukemia (Aml) Carrying Nucleophosmin (Npm1) Gene Mutation", Haematologica, 19th Congress of the European Hematology Association, Milan, Italy Jun. 12, 2014, vol. 99, supplement No. 1 (Jun. 2014).

Casset, et al., "A peptide mimetic of an anti-CD4 monoclonal antibody by rational design", Biochemical and Biophysical Research Communications, 307:198-205, (2003).

Chen, et al., "Selection and Analysis of an Optimized Anti-VEGF Antibody: Crystal Structure of an Affinity-matured Fab in Complex with Antigen", J. Mol. Biol., 293:865-881, (1991).

Choi, et al., "Predicting antibody complementarity determining region structures without classification", Mol. BioSyst., 7, pp. 3327-3334, (2011).

Daver, et al., "Acute myeloid leukemia: advancing clinical trials and promising therapeutics", Expert Rev Hematol., 9(5), pp. 433-445, (May 2016).

De Genst, et al., "Antibody repertoire development in camelids", Developmental and Comparative Immunology, 30, pp. 187-198, (2006).

Drachman, et al., "The next generation of ADCs", Proceedings: AACR 106th Annual Meeting 2015, Cancer Res. 75 (15 Suppl), Abstract SY35-01 (2015).

EPO Application No. 13790467.8 (Published as EP2850104), European Search Report and European Search Opinion, 7 pages, (dated Jun. 14, 2016).

EPO Application No. 17811031.8, European Partial Search Report, 15 pages, (dated Jan. 2, 2020).

EPO Application No. 18171884.2, European Search Report and European Search Opinion, 7 pages, (dated Nov. 23, 2018).

Erba, et al., "A Phase 1b Study of Vadastuximab Talirine in Combination with 7+3 Induction Therapy for Patients with Newly Diagnosed Acute Myeloid Leukemia (AML)", Blood, 128(22), Abstract No. 211, (2016).

Erba, et al., "SGN-CD33A: case reports of anti-leukemic activity and bridge to allogeneic stem cell transplant (SCT) in patients with acute myeloid leukemia (AML)", Biol. Blood Marrow Transplant 21, (suppl 2), S185-186, (2015).

Feldman, et al, Phase III Randomized Multicenter Study of a Humanized Anti-CD33 Monoclonal Antibody, Lintuzumab, in Combination With Chemotherapy, Versus Chemotherapy Alone in Patients With Refractory or First-Relapsed Acute Myeloid Leukemia, Journal of Clinical Oncology, vol. 23, No. 18, pp. 4110-4116, (Jun. 20, 2005).

Feldman, et al., "Novel Therapeutics for Therapy-Related Acute Myeloid Leukemia: 2014", Clinical Lymphoma, Myeloma & Leukemia, vol. 15, No. S1, pp. S91-S93, (2015).

Griffiths, et al., "Human anti-self antibodies with high specificity from phage display libraries", The EMBO Journal, vol. 12, No. 2, pp. 725-734, (1993).

Grunwald, et al., "FL T3 inhibitors for acute myeloid leukemia: a review of their efficacy and mechanisms of resistance", Int J Hematol, 97, pp. 683-694, (2013).

Kennedy, et al., "SGN-CD33A: Preclinical and phase 1 interim clinical trial results of a CD33-directed PBD dimer antibody-drug conjugate for the treatment of acute myeloid leukemia (AML)", Proceedings: AACR 106th Annual Meeting 2015, AACR; Cancer Res. 75 (15 Suppl), Abstract DDT02-04, (Apr. 2015).

Kimka, et al., "Human anti-CD30 recombinant antibodies by guided phage antibody selection using cell panning", British Journal of Cancer, 83(2), pp. 252-260, (2000).

Kindler, et al., "FLT3 as a therapeutic target in AML: still challenging after all these years", Blood, vol. 116, No. 24, pp. 5089-5102, (Dec. 9, 2010).

Kung Sutherland, et al., "SGN-CD33A: a novel CD33-directed antibody-drug conjugate, utilizing pyrrolobenzodiazepine dimers, demonstrates preclinical antitumor activity against multi-drug resistant human AML", ASH Annual Meeting Abstracts 120: Abstract 3589, (2012).

Kung Sutherland, et al., "SGN-CD33A: a novel CD33-targeting antibody-drug conjugate using a pyrrolobenzodiazepine dimer is active in models of drug-resistant AML", Blood, 122:1455-1463, (2013).

Lamminmaki, et al., "Protein Structure and Folding: Crystal Structure of a Recombinant Anti-estradiol Fab Fragment in Complex with 17β-Estradiol", J. Biol. Chem., 276: 36687-36694, (2001).

Laszlo, et al., "Cellular determinants for preclinical activity of a novel CD33/CD3 bispecific T-cell engager (BiTE) antibody, AMG 330, against human AML", Blood, vol. 23, No. 4, 554-561, (Jan. 23, 2014).

Lee, et al., "G-749, a novel FLT3 kinase inhibitor, can overcome drug resistance for the treatment of acute myeloid leukemia", Blood, vol. 123, No. 14, pp. 2209-2219, (Apr. 3, 2014).

Levis, et al., "FLT3 mutations in acute myeloid leukemia: what is the best approach in 2013?", Hematology, American Society of Hematology, pp. 220-226, (2013).

Levy, et al., "A Phase 1b Study of the Combination of Vadastuximab Talirine and 7+3 Induction Th, et al., erapy for Patients With Newly Diagnosed Acute Myeloid Leukemia (AML)", Proceedings of the

(56) References Cited

OTHER PUBLICATIONS

22nd Congress of the European Hematology Association Madrid Spain, Abstract No. S793, (Jun. 25, 2017).
Li, et al., "AMG 925 Is a Dual FLT3/CDK4 Inhibitor with the Potential to Overcome FLT3 Inhibitor Resistance in Acute Myeloid Leukemia", Molecular Cancer Therapeutics, 14(2), pp. 375-383, (Feb. 2015).
MacCallum, et al., "Antibody-antigen Interactions: Contact Analysis and Binding Site Topography", J. Mol. Biol., 262:732-745, (1996).
Meshinchi, et al., "Structural and Functional Alterations of FLT3 in Acute Myeloid Leukemia", Clin Cancer Res 15(13), pp. 4263-4269, (Jul. 1, 2009).
Nand, et al., "A phase 2 trial of azacitidine and gemtuzumab ozogamicin therapy in older patients with acute myeloid leukemia", Blood, 122:3432-3439, (2013).
Ostronoff, et al., "NUP98/NSD1 and FLT3/ITD coexpression is more prevalent in younger AML patients and leads to induction failure: a COG and SWOG report", Blood, 124(15), pp. 2400-2407, (Oct. 9, 2014).
Ostronoff, et al., "NUP98/NSD1 Translocation Further Risk-Stratifies Patients With FLT3/ITD in Acute Myeloid Leukemia: A Report From Children's Oncology Group and SWOG", Blood, 122(21), p. 488, (2013).
Ostronoff, et al., "Prognostic Significance of NPM1 Mutations in the Absence of FLT3-Internal Tandem Duplication in Older Patients With Acute Myeloid Leukemia: A SWOG and UK National Cancer Research Institute/Medical Research Council Report", Journal of Clinical Oncology, vol. 33, No. 10, pp. 1157-1164, (Apr. 1, 2015).
Padlan, et al., "Structure of an antibody-antigen complex: Crystal structure of the HyHEL-10 Fab-lysozyme complex", Proc. Natl. Acad. Sci. USA, 86:5938-5942, (1989).
Pascalis et al., "Grafting of "Abbreviated" Complementarity-Determining Regions Containing Specificity-Determining Residues Essential for Ligand Contact to Engineer a Less Immunogenic Humanized Monoclonal Antibody", J. Immunol., 169:3076-3084, (2002).
PCT Application No. PCT/US2013/041209, International Preliminary Report on Patentability, 7 pages, (dated Apr. 30, 2015).
PCT Application No. PCT/US2013/041209, International Search Report and Written Opinion, 10 pages, (dated Oct. 25, 2013).
PCT Application No. PCT/US2017/022472, International Preliminary Report on Patentability, 8 pages, (dated Sep. 27, 2018).
PCT Application No. PCT/US2017/022472, International Search Report and Written Opinion, 16 pages, (dated Jul. 19, 2017).
PCT Application No. PCT/US2017/027246, International Preliminary Report on Patentability, 8 pages, (dated Oct. 25, 2018).
PCT Application No. PCT/US2017/027246, International Search Report and Written Opinion, 14 pages, (dated Jul. 10, 2017).
PCT Application No. PCT/US2017/035793, International Preliminary Report on Patentability, 7 pages, (dated Dec. 13, 2018).
PCT Application No. PCT/US2017/035793, International Search Report and Written Opinion, 9 pages, (dated Sep. 6, 2017).
PCT Application No. PCT/US2017/036605, International Preliminary Report on Patentability, 11 pages, (dated Dec. 20, 2018).
PCT Application No. PCT/US2017/036605, International Search Report and Written Opinion, 20 pages, (dated Oct. 27, 2017).
Perl, et al., "Selective Inhibition of FLT3 by Gilteritinib in Relapsed/Refractory Acute Myeloid Leukemia: a Multicenter, First-in-human, Open-label, Phase 1/2 Study", Lancet Oncol.,18(8), 1061-1075, (Aug. 2017).
Quentmeier, et al., "FLT3 mutations in acute myeloid leukemia cell lines", Leukemia 17, pp. 120-124, (2003).
Rudikoff, et al., "Single amino acid substitution altering antigen-binding specificity", Proc. Natl. Acad. Sci. USA, 79:1979, (1982).
Seattle Genetics, Inc., Press Release, "Seattle Genetics Presents Phase 1b Data from Vadastuximab Talirine (SGN-CD33A; 33A) in Combination with Standard of Care in Frontline Acute Myeloid Leukemia at ASH Annual Meeting", Available at: https://investor.seattlegenetics.com/press-releases/news-details/2016/Seattle-Genetics-Presents-Phase-1b-Data-from-Vadastuximab-Talirine-SGN-CD33A-33A-in-Combination-with-Standard-of-Care-in-Frontline-Acute-Myeloid-Leukemia-at-ASH-Annual-Meeting/default.aspx, 4 pages, (Dec. 3, 2016).
Seattle Genetics, Inc., Press Release, "Seattle Genetics Discontinues Phase 3 CASCADE Trial of Vadastuximab Talirine (SGN-CD33A) in Frontline Acute Myeloid Leukemia", Available at: https://investor.seattlegenetics.com/press-releases/news-details/2017/Seattle-Genetics-Discontinues-Phase-3-CASCADE-Trial-of-Vadastuximab-Talirine-SGN-CD33A-in-Frontline-Acute-Myeloid-Leukemia/default.aspx, 3 pages, (Jun. 19, 2017).
Stein, et al., "A phase 1 trial of SGN-CD33A as monotherapy in patients with CD33-positive acute myeloid leukemia (AML)", Blood, 126(23), Abstract 324, (Dec. 3, 2015).
Stein, et al., "A phase 1 trial of vadastuximab talirine as monotherapy in patients with CD33-positive acute myeloid leukemia", Blood, vol. 131, No. 4, pp. 387-396, (Jan. 25, 2018).
Stein, et al., "Interim analysis of a phase 1 trial of SGN-CD33A in patients with CD33-positive acute myeloid leukemia (AML)", Blood 124(21), Abstract 623, (2014).
Stein, "Molecularly targeted therapies for acute myeloid leukemia", Hematology, American Society of Hematology, pp. 579-583, (2015).
Stein, et al., "SGN-CD33A (Vadastuximab Talirine) followed by Allogeneic Hematopoietic Stem Cell Transplant (AlloHSCT) Results in Durable Complete Remissions (CRs) in Patients with Acute Myeloid Leukemia (AML)", Abstracts—Biol Blood Marrow Transplant 22 (suppl 3), pp. 211-212, (2016).
Sutherland, et al., "5-azacytidine enhances the anti-leukemic activity of lintuzumab (SGN-33) in preclinical models of acute myeloid leukemia", mAbs, 2:4 440-448, (2010).
Sutherland, et al., "Anti-leukemic activity of lintuzumab (SGN-33) in preclinical models of acute myeloid leukemia", mAbs, 1:5, 481-490, (2009).
Sutherland, et al., "SGN-CD33A: a novel CD33-targeting antibody-drug conjugate using a pyrrolobenzodiazepine dimer is active in models of drug-resistant AML", Blood, vol. 122, No. 8, pp. 1455-1463, (Aug. 2013).
Sutherland, et al., "SGN-CDI 23A, a Pyrrolobenzodiazepine Dimer Linked Anti-CD123 Antibody Drug Conjugate, Demonstrates Effective Anti-Leukemic Activity in Multiple Preclinical Models of AML" Blood, 126:330, available at: http://vw.w.bloodjournal.org/content/126/23/330, (2015).
Sutherland, et al., "SGN-CDI 23A, a Pyrrolobenzodiazepine Dimer Linked Anti-CD123 Antibody Drug Conjugate, Demonstrates Effective Anti-Leukemic Activity in Multiple Preclinical Models of AML", Blood 126:330, (2015).
Tap, et al., "Structure-Guided Blockade of CSF1R Kinase in Tenosynovial Giant-Cell Tumor", New England Journal of Medicine 373;5, pp. 428-437, (Jul. 30, 2015).
Tarlock et al., "Synergistic Effect of SGN-CD33A and FLT3 Inhibitors in FLT3/ITD Acute Myeloid Leukemia", Blood, 132 (Supplement 1): Abstract 2723, (2018).
Tarlock, et al., "2723 Synergistic Effect of SGN-CD33A and FLT3 Inhibitors in FLT3 /ITD Acute Myeloid Leukemia", Oral and Poster Abstracts No. 2723, ASH Annual Meeting, 2 pgs., (Dec. 2, 2018).
Tarlock, et al., "3942 CD33 SNP Genotype and Splice Variation Are Associated with CD33 Cell Surface Expression and SGN-CD33A Pharmacokinetics", Oral and Poster Abstracts No. 3942, ASH Annual Meeting, 2 pgs., (Dec. 3, 2018).
U.S. Appl. No. 13/804,227, Advisory Action dated Nov. 18, 2015.
U.S. Appl. No. 13/804,227, Final Office Action dated Aug. 10, 2015.
U.S. Appl. No. 13/804,227, Non-Final Office Action dated Feb. 18, 2016.
U.S. Appl. No. 13/804,227, Non-Final Office Action dated Feb. 27, 2015.
U.S. Appl. No. 13/804,227, Non-Final Office Action dated Mar. 14, 2016.
U.S. Appl. No. 13/804,227, Restriction Requirement dated Sep. 18, 2014.
U.S. Appl. No. 13/826,007, Non-Final Office Action dated Sep. 11, 2015.
U.S. Appl. No. 14/401,837, Non-Final Office Action dated May 27, 2016.

(56) References Cited

OTHER PUBLICATIONS

U.S. Appl. No. 14/401,837, Notice of Allowance dated Oct. 14, 2016.
Vajdos, et al., "Comprehensive Functional Maps of the Antigen-binding Site of an Anti-ErbB2 Antibody Obtained with Shotgun Scanning Mutagenesis", J. Mol. Biol., 320:415-428, (2002).
Walter, et al., "A Phase 1b Study of Vadastuximab Talirine (33A) in Combination with 7+3 Induction Therapy for Patients with Newly Diagnosed Acute Myeloid Leukemia (AML)", Ann. Hematol. 96, Suppl 1, p. 69, (2017).
Wander, et al., "The evolving role of FLT3 inhibitors in acute myeloid leukemia: quizartinib and beyond", Therapeutic Advances in Hematology, vol. 5(3), pp. 65-77, (2014).
Wang, et al., "CASCADE: A phase 3, randomized, double-blind study of vadastuximab talirine (33A) versus placebo in combination with azacitidine or decitabine in the treatment of older patients with newly diagnosed acute myeloid leukemia (AML)", Journal of Clinical Oncology 35, No. 15 suppl, Abstract TPS7066, 1 pg. (2017).
Ward, et al., "Binding activities of a repertoire of single immunoglobulin variable domains secreted from *Escherichia coli*", Nature, vol. 341, pp. 544-546, (Oct. 12, 1989).
Whiteman, et al., "The Antibody-Drug Conjugate (ADC) IMGN779 Is Highly Active in Vitro and in Vivo Against Acute Myeloid Leukemia (AML) With FLT3-ITD Mutations", Abstract 2321, 56th Annual Meeting of the American-Society-of-Hematology; San Francisco, Ca, USA; 1 pg., (Dec. 6-9, 2014).
Whiteman, et al., "The Antibody-Drug Conjugate (ADC) IMGN779 Is Highly Active in Vitro and in Vivo Against Acute Myeloid Leukemia (AML) With FLT3-ITD Mutations", Blood, vol. 124, No. 21, (Dec. 1, 2014).
Wu, et al., "Humanization of a Murine Monoclonal Antibody by Simultaneous Optimization of Framework and CDR Residues", J. Mol. Biol., 294:151-162, (1999).
Yang, et al., "A Phase 1b Study of Vadastuximab Talirine as Maintenance and in Combination with Standard Consolidation for Patients with Acute Myeloid Leukemia (AML)", Blood, 128(22), Abstract No. 340, (2016).
EPO Application No. 17767412.4, Supplementary Search Report and Search Opinion, 8 pages, (dated Jul. 9, 2019).
EPO Application No. 17783071.8 (Published as EP3442591), European Search Report and European Search Opinion, 9 pages, (dated Oct. 17, 2019).
EPO Application No. 17807611.3, European Supplementary Search Report and Search Opinion, 8 pages, (dated Dec. 18, 2019).
Jeffrey, et al., "Development of Pyrrolobenzodiazepine-Based Antibody-Drug Conjugates for Cancer", AACR Annual Meeting, Abstract No. 4321, 1 pages, (2013).

\* cited by examiner

FIGURE 4

| Compound_name | ADC | Cell_line | Cell line, FLT3 status | Source_short | Bliss Improvement (%) | Bliss PTCDS (%) | Bliss Sig. 3x3 Synergy | Bliss Sig. 3x3 Antagonism | HSA fitted Improvement (%) | HSA fitted PTCDS (%) | HSA fitted Sig. 3x3 Synergy | HSA fitted Sig. 3x3 Antagonism | HSA non-fitted Improvement (%) | HSA non-fitted PTCDS (%) | HSA non-fitted Sig. 3x3 Synergy | HSA non-fitted Sig. 3x3 Antagonism | Loewe Improvement (%) | Loewe PTCDS (%) | Loewe Sig. 3x3 Synergy | Loewe Sig. 3x3 Antagonism | Overall classification |
|---|---|---|---|---|---|---|---|---|---|---|---|---|---|---|---|---|---|---|---|---|---|
| ASP2215 | SGN-CD123A | MOLM13 | mutant | E | 2.4 | 0.7 | 74 | 14 | 8.4 | 0.4 | 107 | 2 | 5.2 | 0.7 | 161 | 0 | 3.4 | 0.8 | 110 | 2 | Synergistic-Additive |
| ASP2215 | SGN-CD123A | MV4-11 | mutant | F | 15.4 | 0.2 | 25 | 9 | 29.8 | -0.6 | 59 | 0 | 30.7 | -1.1 | 89 | 2 | 3.1 | -0.2 | 56 | 0 | Synergistic-Additive |
| ASP2215 | SGN-CD33A | MOLM13 | mutant | E | 1.6 | 0.9 | 50 | 70 | 6.3 | 0.1 | 119 | 18 | 4.2 | 0.8 | 139 | 0 | 5.3 | 0.8 | 119 | 18 | Synergistic-Additive |
| ASP2215 | SGN-CD33A | MV4-11 | mutant | F | 21.8 | 1.6 | 18 | 48 | 39.5 | 0.1 | 53 | 5 | 40.8 | 0.4 | 29 | 0 | 18.5 | 1.5 | 37 | 5 | Synergistic-Additive |
| Crenolanib | SGN-CD33A | MOLM13 | mutant | E | 6.3 | 1.0 | 74 | 25 | 13.7 | 0.6 | 105 | 0 | 4.4 | 0.9 | 151 | 0 | 5.3 | 1.0 | 109 | 0 | Synergistic |
| Crenolanib | SGN-CD33A | MV4-11 | mutant | F | 2.5 | 0.8 | 50 | 13 | 34.2 | -2.7 | 89 | 1 | 14.1 | -2.1 | 69 | 0 | 3.2 | 0.5 | 86 | 40 | Synergistic |
| G-749 | SGN-CD33A | MOLM13 | mutant | E | 8.0 | 0.7 | 61 | 52 | 26.6 | 1.7 | 132 | 0 | 25.7 | 1.7 | 130 | 0 | 7.5 | 1.1 | 134 | 0 | Synergistic |
| G-749 | SGN-CD33A | MV4-11 | mutant | H | n/a | n/a | n/a | n/a | n/a | n/a | n/a | n/a | 0.5 | n/a | 1 | 10 | n/a | -2.1 | n/a | n/a | Synergistic |
| Midostaurin | SGN-CD33A | MOLM13 | mutant | H | 9.5 | 1.5 | 20 | 54 | 20.3 | -0.9 | 61 | 0 | 19.6 | 0.3 | 42 | 0 | 7.7 | 1.3 | 48 | 23 | Synergistic |
| Midostaurin | SGN-CD33A | MV4-11 | mutant | H | 2.2 | -0.3 | 43 | 88 | 11.4 | 1.5 | 121 | 1 | 4.9 | 1.5 | 114 | 0 | 5.2 | 1.1 | 116 | 1 | Synergistic |
| Quizartinib | SGN-CD123A | MOLM13 | mutant | H | 8.9 | 0.4 | 44 | 69 | 24.5 | 1.7 | 138 | 0 | 4.3 | 1.8 | 131 | 0 | 9.1 | 1.1 | 142 | 0 | Synergistic |
| Quizartinib | SGN-CD123A | MV4-11 | mutant | H | 3.3 | 0.0 | 38 | 101 | 13.7 | 1.6 | 149 | 0 | 13.7 | 1.6 | 146 | 0 | 7.3 | 1.4 | 143 | 0 | Synergistic |
| Quizartinib | SGN-CD33A | MOLM13 | mutant | H | 14.5 | 1.0 | 62 | 44 | 28.5 | 1.4 | 139 | 0 | 29.3 | 1.5 | 125 | 0 | 6.6 | 0.9 | 136 | 0 | Synergistic |
| Quizartinib | SGN-CD33A | MV4-11 | mutant | H | 1.9 | -0.1 | 37 | 100 | 11.6 | 1.2 | 141 | 0 | 4.8 | 1.2 | 121 | 0 | 7.3 | 1.1 | 137 | 0 | Synergistic |
| Quizartinib | SGN-CD123A | MOLM13 | mutant | H | 17.8 | 1.7 | 75 | 43 | 31.3 | 2.0 | 112 | 0 | 33.7 | 2.1 | 101 | 0 | 14.4 | 1.5 | 113 | 0 | Synergistic |
| Quizartinib | SGN-CD123A | MV4-11 | mutant | F | 14.4 | 0.9 | 69 | 75 | 19.8 | 1.7 | 127 | 0 | 19.2 | 1.7 | 137 | 0 | 13.5 | 1.5 | 122 | 0 | Synergistic |
| Quizartinib | SGN-CD123A | MOLM13 | mutant | H | n/a | n/a | n/a | n/a | n/a | n/a | n/a | n/a | 10.1 | n/a | 24 | 34 | n/a | -1.3 | n/a | n/a | Additive |
| Quizartinib | SGN-CD123A | MV4-11 | mutant | F | 3.3 | -0.4 | 23 | 19 | 4.1 | -2.6 | 54 | 0 | 2.1 | n/a | 9 | 42 | 3.7 | -1.2 | 53 | 6 | Additive |
| Quizartinib | SGN-CD33A | MOLM13 | mutant | H | 12.6 | 0.6 | 34 | 90 | 25.1 | 1.4 | 146 | 0 | 23.4 | 1.4 | 153 | 0 | 8.6 | 0.9 | 149 | 0 | Synergistic-Additive |

| Drug | Antibody | Cell line | | | | | | | | | | | | | | | | | | Result |
|---|---|---|---|---|---|---|---|---|---|---|---|---|---|---|---|---|---|---|---|---|
| ASP2215 | | MV4-11 | F | 11.9 | 0.5 | 17 | 80 | 11.1 | -0.4 | 35 | 55 | 6.0 | -0.6 | 51 | 0 | 10.5 | 0.3 | 31 | 55 | Synergistic-Additive |
| | SGN-CD123A | Kasumi1 | H | 9.5 | -0.3 | 22 | 124 | 22.6 | 1.6 | 128 | 0 | 7.6 | 1.6 | 119 | 0 | 9.5 | 1.3 | 123 | 0 | Additive |
| | | TF1a | E | 3.2 | 5.4 | 4 | 0 | 23.4 | 1.1 | 18 | 0 | 25.2 | 4.4 | 14 | 0 | 23.4 | 4.8 | 15 | 14 | Additive |
| | SGN-CD33A | Kasumi1 | E | 18.6 | -1.4 | 27 | 4 | 18.2 | 7.7 | 14 | 13 | 0.5 | -2.9 | 8 | 0 | 15.1 | -2.1 | 7 | 3 | Additive |
| | | ME-1 | E | 2.0 | -0.5 | 4 | 0 | 18.8 | -3.0 | 18 | 3 | n/a | -1.6 | 0 | 0 | 16.4 | -0.7 | 19 | 15 | |
| | | KG-1_8031 | H | n/a | -4.5 | 0 | 59 | 17.8 | -0.2 | 19 | 11 | 18.4 | -0.2 | 2 | 25 | 12.7 | -0.8 | 17 | 35 | Antagonistic |
| | | KG-1_cb | H | 12.7 | -13 | 0 | 80 | 14.3 | -7.2 | 5 | 26 | 13.9 | -7.2 | 4 | 37 | 14.3 | -8.5 | 5 | 78 | Antagonistic |
| | | ME-1 | H | n/a | -4.2 | 2 | 36 | n/a | -9.3 | 0 | 70 | n/a | -9.8 | 0 | 45 | n/a | -11 | 0 | 107 | Antagonistic |
| | | TF1a | E | n/a | -94 | 0 | 151 | n/a | -56 | 0 | 100 | n/a | -58 | 0 | 0 | n/a | -58 | 0 | 68 | Antagonistic |
| | | THP-1 | H | n/a | -6.1 | 0 | 36 | 22.8 | -4.4 | 6 | 62 | 21.5 | -7.1 | 6 | 47 | 22.8 | -7.4 | 5 | 93 | |
| Crenolanib | | TF1a | E | 9.8 | -17 | 0 | 76 | 22.4 | -19 | 3 | 90 | 19.2 | -19 | 4 | 20 | 19.1 | -20 | 3 | 34 | Antagonistic |
| | | THP-1 | H | -3.3 | -3.3 | 8 | 39 | 3.5 | -1.6 | 1 | 32 | n/a | -2.2 | 0 | 57 | 3.5 | -2.0 | 1 | 24 | Antagonistic |
| | SGN-CD33A | Kasumi1 | H | -9.5 | -9.5 | 0 | 119 | 14.6 | -1.1 | 29 | 19 | 10.8 | -1.2 | 5 | 2 | 10.1 | -1.7 | 24 | 19 | Antagonistic |
| G-749 | | KG-1_8031 | H | 10.3 | -2.3 | 7 | 8 | 22.4 | -1.5 | 14 | 16 | 21.1 | -1.3 | 14 | 70 | 17.2 | -2.8 | 12 | 62 | Additive |
| | | KG-1_cb | H | 23.8 | -2.1 | 10 | 7 | 35.8 | -7.9 | 6 | 92 | 34.8 | -7.8 | 9 | 54 | 30.3 | -9.0 | 4 | 94 | Antagonistic |
| | | ME-1 | H | n/a | -274 | 0 | 103 | n/a | -190 | 0 | 65 | n/a | -215 | 0 | 57 | n/a | -192 | 0 | 65 | Antagonistic |
| | | TF1a | E | n/a | -19 | 0 | 85 | 18.9 | -23 | 3 | 102 | n/a | -24 | 0 | 70 | 14.6 | -25 | 2 | 103 | Antagonistic |
| | | THP-1 | H | 7.8 | -11 | 20 | 61 | 4.3 | -7.7 | 6 | 61 | n/a | -8.6 | 0 | 54 | 4.3 | -8.1 | 6 | 62 | Antagonistic |
| Midostaurin | | Kasumi1 | H | 2.3 | -5.1 | 10 | 83 | 14.9 | -0.4 | 34 | 20 | 14.1 | -0.3 | 28 | 2 | 14.2 | -0.9 | 32 | 21 | Antagonistic |
| | | KG-1_8031 | H | 2.0 | -8.3 | 7 | 83 | 20.9 | -1.7 | 24 | 18 | 20.6 | -1.7 | 26 | 1 | 20.9 | -2.7 | 17 | 21 | Antagonistic |
| | | KG-1_cb | H | n/a | -4.8 | 0 | 20 | 17.2 | -6.6 | 2 | 57 | n/a | -6.5 | 0 | 0 | 15.4 | -7.6 | 2 | 61 | Antagonistic |
| | | ME-1 | H | n/a | -50 | 0 | 130 | n/a | -30 | 0 | 102 | n/a | -32 | 0 | 38 | n/a | -30 | 0 | 109 | Antagonistic |
| | | TF1a | H | n/a | -17 | 0 | 82 | 23.7 | -13 | 8 | 74 | 24.4 | -13 | 17 | 79 | 23.7 | -14 | 5 | 76 | Antagonistic |
| | | THP-1 | H | n/a | -2.2 | 0 | 18 | 13.2 | -1.3 | 0 | 16 | 0.5 | -1.5 | 10 | 4 | n/a | -1.5 | 0 | 18 | Additive |
| Quizartinib | SGN-CD33A | Kasumi1 | H | -7.3 | -7.3 | 0 | 100 | 13.2 | -0.8 | 35 | 13 | 15.8 | -0.8 | 3 | 2 | 10.9 | -1.4 | 31 | 15 | Additive |
| | | KG-1_8031 | H | 7.6 | -6.6 | 3 | 89 | 23.8 | -0.4 | 13 | 29 | 25.6 | -0.4 | 13 | 0 | 23.8 | -1.4 | 12 | 34 | Antagonistic |
| | | KG-1_cb | H | 7.3 | -1.0 | 5 | 26 | 13.0 | -6.8 | 14 | 70 | 13.2 | -7.1 | 5 | 27 | 10.7 | -8.0 | 13 | 77 | Antagonistic |
| | | ME-1 | H | n/a | -64 | 0 | 122 | 23.2 | -19 | 5 | 38 | n/a | -22 | 0 | 14 | 23.2 | -21 | 5 | 42 | Antagonistic |
| | | TF1a | H | 31.7 | -3.5 | 19 | 32 | 37.1 | -6.8 | 25 | 62 | 42.0 | -6.9 | 17 | 20 | 29.2 | -8.0 | 26 | 62 | Antagonistic |
| | | THP-1 | H | 3.3 | -5.1 | 1 | 39 | 13.9 | -2.8 | 0 | 28 | n/a | -2.8 | 0 | 27 | 12.8 | -2.9 | 3 | 29 | Antagonistic |
| | SGN-CD33A | Kasumi1 | H | 2.7 | -3.8 | 0 | 84 | 23.4 | 3.2 | 86 | 1 | 20.7 | 3.2 | 43 | 0 | 17.2 | 2.6 | 83 | 1 | Additive |
| | | KG-1_8031 | H | n/a | -6.9 | 0 | 38 | 19.5 | 0.1 | 33 | 28 | 20.3 | 0.8 | 21 | 27 | 19.5 | -1.1 | 29 | 31 | Antagonistic |
| | | KG-1_cb | H | n/a | -42 | 0 | 126 | 10.1 | -27 | 5 | 83 | 8.9 | -26 | 2 | 54 | 10.1 | -28 | 5 | 91 | Antagonistic |
| | | ME-1 | H | n/a | -202 | 0 | 153 | n/a | -85 | 0 | 74 | n/a | -92 | 0 | 72 | n/a | -88 | 0 | 79 | Antagonistic |
| | | TF1a | H | 23.8 | -16 | 17 | 82 | 37.6 | -8.4 | 19 | 87 | 36.0 | -9.1 | 20 | 62 | 37.6 | -10 | 18 | 87 | Antagonistic |
| | | THP-1 | H | 5.0 | -1.0 | 7 | 38 | 4.7 | 0.5 | 6 | 5 | 8.9 | 0.5 | 0 | 2 | 4.7 | 0.4 | 6 | 5 | Additive | wild type

FIGURE 4 (cont.)

COMBINATIONS OF PBD-BASED ANTIBODY DRUG CONJUGATES WITH FLT3 INHIBITORS

CROSS-REFERENCES TO RELATED APPLICATIONS

This application is a U.S. nation stage filing under 35 U.S.C. § 371 of International Application No. PCT/US2017/036605, filed Jun. 8, 2017, which claims the benefit of U.S. Provisional Application No. 62/347,758 filed Jun. 9, 2016, U.S. Provisional Application No. 62/356,909 filed Jun. 30, 2016 and U.S. Provisional Application No. 62/490,334 filed Apr. 26, 2017, each of which are hereby incorporated by reference in their entirety for all purposes.

FIELD OF THE INVENTION

This invention relates to treatment of cancer using an antibody drug conjugate comprising a PBD cytotoxic agent in combination with FLT3 inhibitors.

BACKGROUND OF THE INVENTION

Antibody drug conjugates (ADCs) have been shown to be effective at delivering cytotoxic agents to cells that express an antigen recognized by the antibody component of the ADC, e.g., cancer cells. While ADCs have demonstrated activity in the clinic, not all patients respond to single agent ADCs. This application solves these and other problems.

BRIEF SUMMARY OF THE INVENTION

This disclosure provides a method of treating cancer by administering an antibody drug conjugate (ADC) and a FLT3 inhibitor. The ADC comprises an antibody that binds to an antigen on a cancer cell and a PBD cytotoxic agent. Antibodies are antibodies that specifically bind to proteins expressed on cancer cells, e.g., CD33, CD123, CD19, CD70, and CD352. Exemplary FLT3 inhibitors are midostaurin, quizartinib, crenolanib, gilteritinib, FLX-925 also known as AMG-925, and G-749.

The PBD cytotoxic agent has the formula

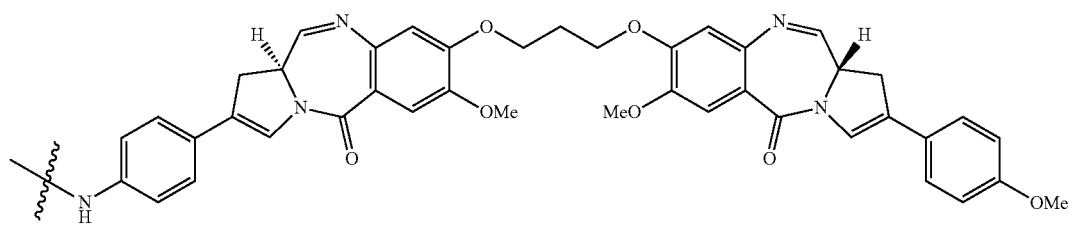 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

A formula of the an antibody (Ab) conjugated to the PBD molecule, including a linker has the formula

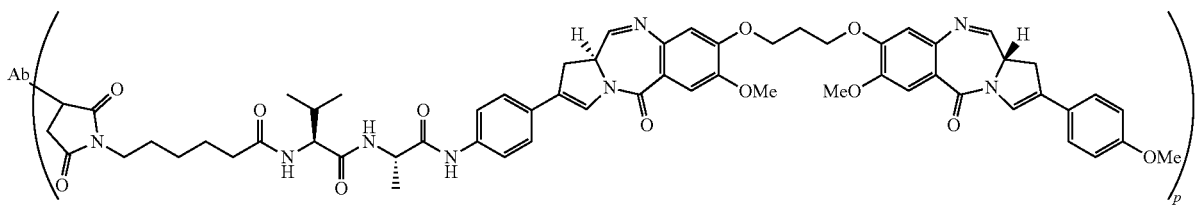

In one embodiment the ADC that includes a PBD cytotoxic agent is administered with the FLT3 inhibitor midostaurin. In another embodiment, the ADC that includes a PBD cytotoxic agent is administered with the FLT3 inhibitor quizartinib. In another embodiment, the ADC that includes a PBD cytotoxic agent is administered with the FLT3 inhibitor crenolanib. In another embodiment, the ADC that includes a PBD cytotoxic agent is administered with the FLT3 inhibitor gilteritinib. In another embodiment, the ADC that includes a PBD cytotoxic agent is administered with the FLT3 inhibitor G-749. In a further embodiment, the ADC that includes a PBD cytotoxic agent is administered with FLX-925 also known as AMG-925.

In one embodiment, the ADC includes a PBD agent and an antibody that specifically binds to the human CD33 protein. This ADC is administered in combination with an FLT3 inhibitor to treat cancer in a subject that has a CD33 positive cancer. In a further embodiment, the antibody is a h2H12 antibody. In another embodiment, the antibody is a h2H12EC antibody. In another embodiment, the FLT3 inhibitor is midostaurin, quizartinib, crenolanib, gilteritinib, FLX-925 also known as AMG-925, or G-749. In a further embodiment, the CD33 positive cancer is acute myeloid leukemia or myelodysplastic syndrome.

In one embodiment, the ADC includes a PBD agent and an antibody that specifically binds to the human CD123 protein. This ADC is administered in combination with an FLT3 inhibitor to treat cancer in a subject that has a CD123 positive cancer. In a further embodiment, the antibody is the h7G3 antibody. In another embodiment, the antibody is a h7G3EC antibody. In another embodiment, the FLT3 inhibitor is midostaurin, quizartinib, crenolanib, gilteritinib, FLX-925 also known as AMG-925, or G-749. In a further embodiment, the CD33 positive cancer is acute myeloid leukemia or myelodysplastic syndrome.

Definitions

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote an immunoglobulin protein produced by the body in response to the presence of an antigen and that bind to the antigen. The term also includes antigen-binding fragments and engineered variants thereof. Hence, the term "antibody" includes, for example, intact monoclonal antibodies comprising full-length immunoglobulin heavy and light chains (e.g., antibodies produced using hybridoma technology) and antigen-binding antibody fragments, such as F(ab')2 and Fab fragments. Genetically engineered intact antibodies and fragments, such as chimeric antibodies, humanized antibodies, single-chain Fv fragments, single-chain antibodies, diabodies, minibodies, linear antibodies, multivalent and multispecific (e.g., bispecific) hybrid antibodies, and the like, are also included. Thus, the term "antibody" is used expansively to include any protein that comprises an antigen-binding site of an antibody and is capable of specifically binding to its antigen.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum size of such a region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362: 367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')2, F(ab)c, diabodies, dAbs, minibodies, nanobodies, Fab-scFv fusions, bispecific (scFv)4-IgG, and bispecific (scFv)2-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function, see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 Kd or 214 amino acids) are encoded by a variable region gene at the amino-terminus (encoding about 110 amino acids) and by a kappa or lambda constant region gene at the carboxyl-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally *Fundamental Immunology* (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The term "chimeric antibody" refers to an antibody having variable domains derived from a first species and constant regions derived from a second species. Chimeric immunoglobulins or antibodies can be constructed, for example by genetic engineering, from immunoglobulin gene segments belonging to different species. The term "humanized antibody," as defined infra, is not intended to encompass chimeric antibodies. Although humanized antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

The term "humanized VH domain" or "humanized VL domain" refers to an immunoglobulin VH or VL domain comprising some or all CDRs entirely or substantially from a non-human donor immunoglobulin (e.g., a mouse or rat) and variable region framework sequences entirely or substantially from human immunoglobulin sequences. The non-human immunoglobulin providing the CDRs is called the "donor" and the human immunoglobulin providing the framework is called the "acceptor." In some instances, humanized antibodies may retain non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular, variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least 85%, at least 90%, at least 95%, or 100% of corresponding residues defined by Kabat are identical. Hence, all parts of a humanized antibody, except possibly the CDRs, are entirely or substantially from corresponding parts of natural human immunoglobulin sequences.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

With regard to proteins as described herein, reference to amino acid residues corresponding to those specified by SEQ ID NO includes post-translational modifications of such residues.

The term "anti-CD33 antibody" refers to an antibody that specifically binds to the human CD33 protein. In a preferred embodiment the anti-CD33 antibody comprises the CDRs of the light chain variable region of SEQ ID NO: 1 and the CDRs of the heavy chain variable region of SEQ ID NO:2. In another preferred embodiment, the anti-CD33 antibody comprises the light chain variable region of SEQ ID NO: 1 and the heavy chain variable region of SEQ ID NO:2. In other preferred embodiments the anti-CD33 antibody includes a human constant region and is an IgG1 antibody. In another preferred embodiment, the anti-CD33 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD123 antibody" refers to an antibody that specifically binds to the human CD123 protein. In a preferred embodiment the anti-CD123 antibody comprises the CDRs of the light chain variable region of SEQ ID NO:9 and the CDRs of the heavy chain variable region of SEQ ID NO:8. In another preferred embodiment, the anti-CD123 antibody comprises the light chain variable region of SEQ ID NO:9 and the heavy chain variable region of SEQ ID NO:8. In other preferred embodiments the anti-CD123 antibody includes a human constant region and is an IgG1 antibody. In another preferred embodiment, the anti-CD123 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD19 antibody" refers to an antibody that specifically binds to the human CD19 protein. In a preferred embodiment the anti-CD19 antibody comprises the CDRs of the light chain variable region of SEQ ID NO: 10 and the CDRs of the heavy chain variable region of SEQ ID NO: 11. In another preferred embodiment, the anti-CD19 antibody comprises the light chain variable region of SEQ ID NO: 10 and the heavy chain variable region of SEQ ID NO:11. In other preferred embodiments the anti-CD19 antibody includes a human constant region and is an IgG1 antibody. In another preferred embodiment, the anti-CD19 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD70 antibody" refers to an antibody that specifically binds to the human CD70 protein. In a preferred embodiment the anti-CD70 antibody comprises the CDRs of the light chain variable region of SEQ ID NO: 12 and the CDRs of the heavy chain variable region of SEQ ID NO: 13. In another preferred embodiment, the anti-CD70 antibody comprises the light chain variable region of SEQ ID NO: 12 and the heavy chain variable region of SEQ ID NO: 13. In other preferred embodiments the anti-CD70 antibody includes a human constant region and is an IgG1 antibody. In another preferred embodiment, the anti-CD70 antibody comprises a heavy chain constant region with an S239C substitution using the EU index according to Kabat for amino acid numbering. Examples of such heavy chain constant regions are shown in, e.g., SEQ ID NOs:6 and 7.

The term "anti-CD352 antibody" refers to an antibody that specifically binds to the human CD352 protein. In a preferred embodiment the anti-CD352 antibody comprises the CDRs of the light chain variable region of SEQ ID NO: 14 and the CDRs of the heavy chain variable region of SEQ ID NO: 15. In another preferred embodiment, the anti-CD352 antibody comprises the light chain variable region of SEQ ID NO: 14 and the heavy chain variable region of SEQ ID NO: 15. In other preferred embodiments the anti-CD70 antibody includes a human constant region and is an IgG1 antibody. In another preferred embodiment, the anti-CD352 antibody comprises a heavy chain constant region with an S239C substitution using the EU index according to Kabat for amino acid numbering. Examples of such heavy chain constant regions are shown in, e.g., SEQ ID NOs:6 and 7.

An antibody-drug conjugate (ADC) is an antibody conjugated to a cytotoxic drug typically via a linker. The linker may comprise a cleavable unit or may be non-cleavable. Cleavable units include, for example, disulfide-containing linkers that are cleavable through disulfide exchange, acid-labile linkers that are cleavable at acidic pH, and linkers that are cleavable by hydrolases, esterases, peptidases, and glucoronidases (e.g., peptide linkers and glucuronide linkers). Non-cleavable linkers are believed to release drug via a proteolytic antibody degradation mechanism.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

The term "administration route" includes art-recognized administration routes for delivering a therapeutic protein such as, for example, parenterally, intravenously, intramuscularly, or subcutaneously. For administration of an ADC for the treatment of cancer, administration into the systemic circulation by intravenous or subcutaneous administration may be desired. For treatment of a cancer characterized by a solid tumor, administration can also be localized directly into the tumor, if so desired.

The term "treatment" refers to the administration of a therapeutic agent to a patient, who has a disease, with the purpose to cure, heal, alleviate, delay, relieve, alter, remedy, ameliorate, improve or affect the disease.

The term "patient" includes human and other mammalian subjects that receive either prophylactic or therapeutic treatment.

The term "effective amount," "effective dose," or "effective dosage" refers to an amount that is sufficient to achieve or at least partially achieve the desired effect, e.g., sufficient to inhibit the occurrence or ameliorate one or more symptoms of a disease or disorder. An effective amount of a pharmaceutical composition is administered in an "effective regime." The term "effective regime" refers to a combination of amount of the composition being administered and dosage frequency adequate to accomplish prophylactic or therapeutic treatment of the disease or disorder.

The term "dosage unit form" (or "unit dosage form") as used herein refers to a physically discrete unit suitable as unitary dosages for a patient to be treated, each unit containing a predetermined quantity of active compound (an ADC in accordance with the present invention) calculated to produce the desired therapeutic effect in association with the required pharmaceutical carrier, diluent, or excipient. The specification for the dosage unit forms of the invention are dictated by and directly dependent on the unique characteristics of the active compound and the particular therapeutic effect to be achieved, and the limitations inherent in the art of compounding such an active compound for the treatment of patients.

Actual dosage levels of an ADC in a formulation of the present invention may be varied so as to obtain an amount of the ADC that is effective to achieve a desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well-known in the medical arts.

The phrase "pharmaceutically acceptable salt," as used herein, refers to pharmaceutically acceptable organic or inorganic salts of a compound. The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

A "cytotoxic effect" refers to the depletion, elimination and/or the killing of a target cell. A "cytotoxic agent" refers to an agent that has a cytotoxic effect on a cell.

A "cytostatic effect" refers to the inhibition of cell proliferation. A "cytostatic agent" refers to an agent that has a cytostatic effect on a cell, thereby inhibiting the growth and/or expansion of a specific subset of cells.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention, i.e., the EU index according to Kabat. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "pharmaceutical formulation" refers to a preparation which is in such form as to permit the biological activity of the active ingredient to be effective (when administered to a subject), and which contains no additional components which are unacceptably toxic to a subject to which the formulation would be administered. Such formulations are sterile.

Compositions or methods "comprising" one or more recited elements may include other elements not specifically recited.

Reference to a numerical range herein (e.g., "X to Y" or "from X to Y") includes the endpoints defining the range and all values falling within the range.

As used herein, the term "about" denotes an approximate range of plus or minus 10% from a specified value. For instance, the language "about 20%" encompasses a range of 18-22%. As used herein, about also includes the exact amount. Hence "about 20%" means "about 20%" and also "20%."

BRIEF DESCRIPTION OF THE DRAWINGS

FIG. 3A provides a comparison of the count of antagonistic (y-axis) and synergistic (x-axis) 3×3 dose blocks with p-values less than 0.01 according to the Loewe additivity model. FIG. 3B provides box plots of antagonistic and synergistic count of 3×3 dose blocks for each combination-FLT3 status group according to the Loewe Additivity model.

FIG. 3C provides p-Values of comparisons between FLT3 wild type and FLT3 mutant cell lines for treatment with PBD ADCs in combination with FLT3 inhibitors. FIG. 3D shows statistically significant synergistic and antagonistic 3×3 dose blocks for PBD-ADCs combined with FLT3 inhibitors or HMAs.

FIG. 4 shows the data for the cytotoxicity assays.

DETAILED DESCRIPTION

Figure 1A:
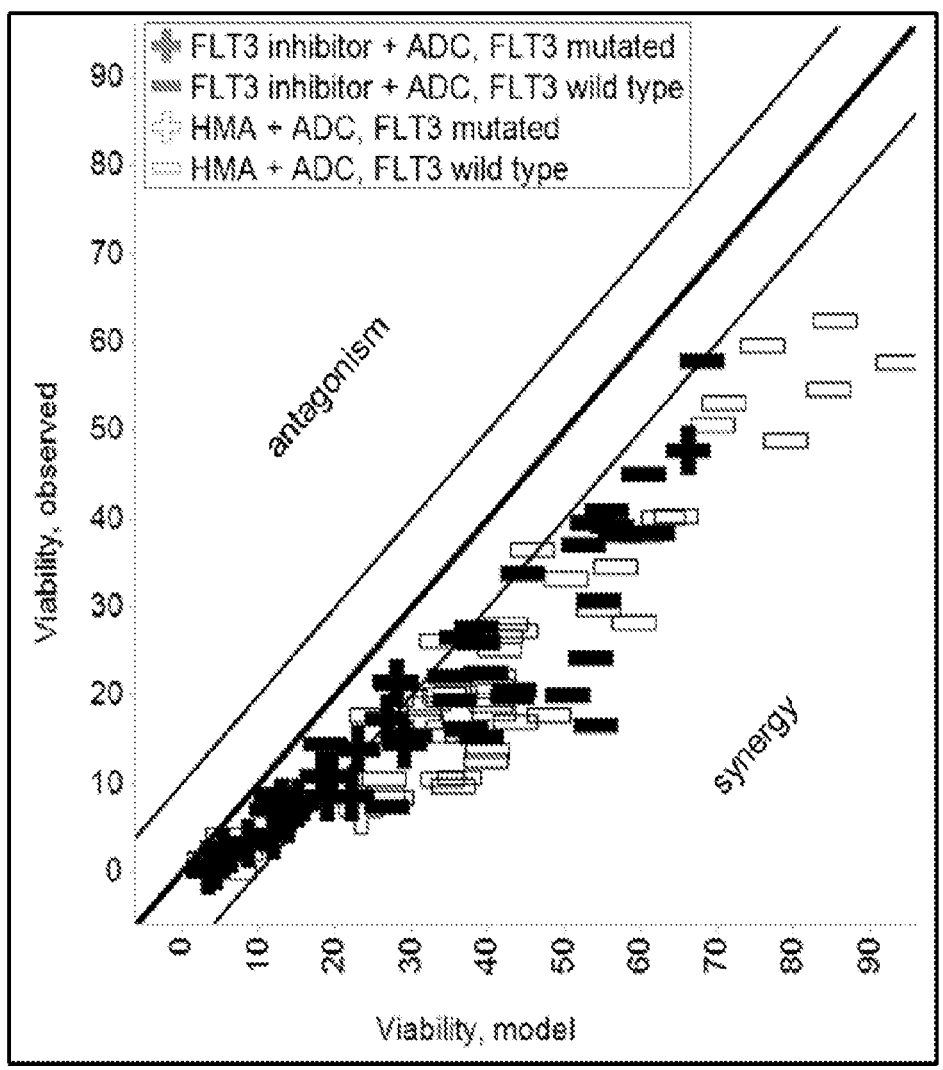
FIGS. 1A and 1B show cytotoxicity for PBD-ADCs combined with FLT3 Inhibitors or hypomethylating agents (HMAs).

This disclosure demonstrates for the first time, that an ADC conjugated to a PBD, exhibits synergy when combined with a FLT3 inhibitor, e.g., midostaurin, quizartinib, crenolanib, gilteritinib, FLX-925 also known as AMG-925, or G-749.

I. Antibody Drug Conjugates

A. Antibodies

Antibodies that are part of antibody drug conjugates specifically bind to proteins that are expressed on cancer cells. In preferred embodiments, the proteins or epitopes bound by the antibodies are expressed on the external part of the cancer cell, e.g. are an external part of a transmembrane protein or are attached to the cell through a glycolipid anchor. The proteins bound by the antibody component of an ADC are preferably not expressed in non-cancerous cells or tissues or are expressed at higher levels in cancerous cells or tissues as compared to non-cancerous cells or tissues. Antibodies include, e.g., Fv, single-chain Fv (scFv), Fab, Fab', F(ab')2, F(ab)c, diabodies, dAbs, minibodies, nanobodies, Fab-scFv fusions, bispecific (scFv)4-IgG, and bispecific (scFv)2-Fab. In some aspects, the cysteine residue is substituted for serine in the antibody at position 239 (IgG) as determined by the EU index (Kabat, Sequences of Proteins of Immunological Interest (National Institutes of Health, Bethesda, Md., 1987 and 1991). This cysteine substitution is referred to herein as S239C.

a. Anti-CD33 Antibodies

The anti-CD33 antibody disclosed herein is the humanized 2H12 antibody (h2H12). The murine 2H12 antibody was raised in mice, using the human CD33 protein as an immunogen. After making hybridomas from the spleens of the immunized mice, followed by screening for CD33 binding activity, the murine 2H12 antibody was selected for humanization. The h2H12 antibody was derived from the murine 2H12 antibody. The humanization procedure is disclosed in PCT publication WO 2013/173,496; which is herein incorporated by reference for all purposes. The variable region sequences of the h2H12 light and heavy chains are provided as SEQ ID NO:1 and SEQ ID NO:2, respectively.

The h2H12 antibody comprises human constant regions. Sequences of human constant regions are provided in the sequence listing. The heavy chain constant region of h2H12 includes a substitution mutation, S239C (numbering EU according to Kabat), to facilitate conjugation of a drug-linker to the antibody. The sequence of a human constant region comprising the S239C mutation is provided at SEQ ID NOs:6 and 7. The h2H12 antibody comprising the S239C mutation is also referred to as h2H12EC.

b. Anti-CD123 Antibodies

The anti-CD123 antibody disclosed herein is the humanized 7G3 antibody (h7G3). The h7G3 antibody binds to the human CD123 protein was derived from the murine 7G3 antibody. The humanization procedure is disclosed in U.S. Ser. No. 62/175,121; which is herein incorporated by reference for all purposes. The variable region sequences of the h7G3 heavy and light chains are provided as SEQ ID NO:8 and SEQ ID NO:9, respectively.

The h7G3 antibody comprises human constant regions. Sequences of human constant regions are provided in the sequence listing. The heavy chain constant region of h7G3 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The h7G3 antibody comprising the S239C mutation is also referred to as h7G3EC.

c. Anti-CD19 Antibodies

The anti-CD19 antibody disclosed herein is the humanized BU12 antibody (hBU12). The hBU12 antibody binds to the human CD19 protein and was derived from the murine BU12 antibody. The humanization procedure is disclosed in WO2009/052431; which is herein incorporated by reference for all purposes. The variable region sequences of the hBU12 light and heavy chains are provided as SEQ ID NO:10 and SEQ ID NO:11, respectively.

The hBU12 antibody comprises human constant regions. Sequences of human constant regions are provided in the sequence listing. The heavy chain constant region of hBU12 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The hBU12 antibody comprising the S239C mutation is also referred to as hBU12EC.

d. Anti-CD70 Antibodies

The anti-CD70 antibody disclosed herein is the humanized 1F6 antibody (h1F6). The h1F6 antibody binds to the human CD70 protein and was derived from the murine 1F6 antibody. The humanization procedure is disclosed in WO2006/113,909; which is herein incorporated by reference for all purposes. The variable region sequences of the h1F6 light and heavy chains are provided as SEQ ID NO:12 and SEQ ID NO:13, respectively.

The h1F6 antibody comprises human constant regions. Sequences of human constant regions are provided in the sequence listing. The heavy chain constant region of h1F6 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The h1F6 antibody comprising the S239C mutation is also referred to as h1F6EC.

e. Anti-CD352 Antibodies

The anti-CD352 antibody disclosed herein is the humanized 20F3 antibody (h20F3). The h20F3 antibody binds to the human CD70 protein and was derived from the murine 20F3 antibody. The humanization procedure is disclosed in U.S. Ser. No. 62/186,596 and U.S. Ser. No. 62/321,849; which are herein incorporated by reference for all purposes. The variable region sequences of the h20F3 light and heavy chains are provided as SEQ ID NO:14 and SEQ ID NO:15, respectively.

The h20F3 antibody comprises human constant regions. Sequences of human constant regions are provided in the sequence listing. The heavy chain constant region of h20F3 includes a substitution mutation, S239C (numbering of EU index according to Kabat), to facilitate conjugation of a drug-linker to the antibody. The sequence of a human constant region comprising the S239C mutation is provided at SEQ ID NOs:6 and 7. The h20F3 antibody comprising the S239C mutation is also referred to as h20F3EC.

B. Drug Linkers

Exemplary CD33 antibody-drug conjugates include PBD based antibody-drug conjugates; i.e., antibody-drug conjugates wherein the drug component is a PBD drug.

PBDs are of the general structure:

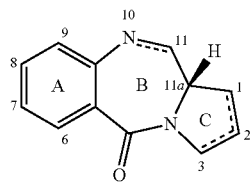

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). The ability of PBDs to form an adduct in the minor groove enables them to interfere with DNA processing, hence their use as antitumour agents.

The biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

In some embodiments, PBD based antibody-drug conjugates comprise a PBD dimer linked to an anti-CD33 antibody. The monomers that form the PBD dimer can be the same or different, i.e., symmetrical or unsymmetrical. The PBD dimer can be linked to the anti-CD33 antibody at any position suitable for conjugation to a linker. For example, in some embodiments, the PBD dimer will have a substituent at the C2 position that provides an anchor for linking the compound to an antibody. In alternative embodiments, the N10 position of the PBD dimer will provide the anchor for linking the compound to an antibody.

Typically the PBD based antibody-drug conjugate comprises a linker between the PBD drug and an antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

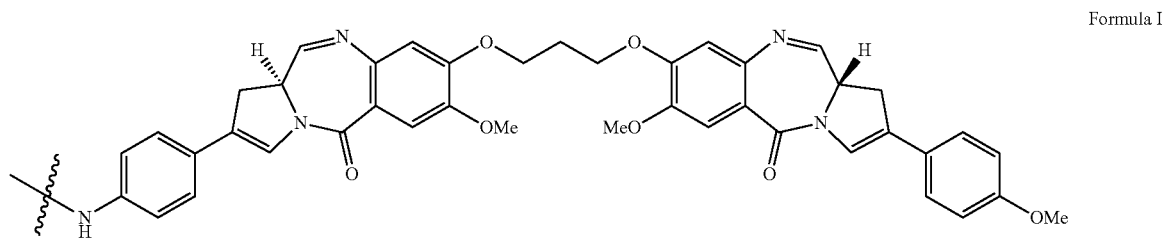 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

Formula I or a pharmaceutically acceptable salt thereof. An exemplary linker is as follows wherein the wavy line indicates the site of attachment to the drug and the antibody is linked via the maleimide group.

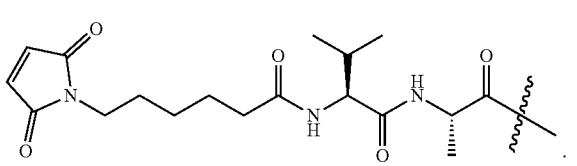

Formula 2

Exemplary PBDs based antibody-drug conjugates include antibody-drug conjugates as shown below wherein Ab is an antibody as described herein:

Formula 3

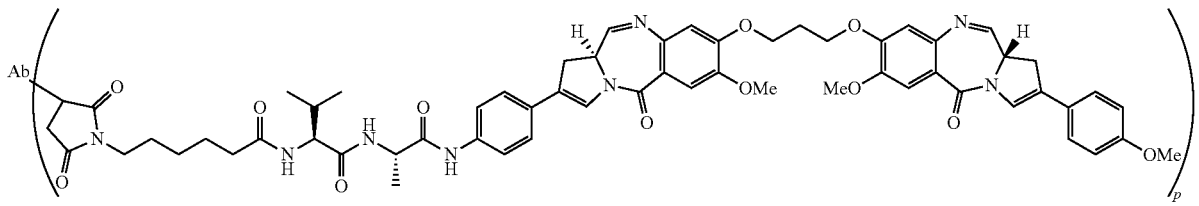

or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the drug linker via a sulfur atom of a cysteine residue that is engineered into the antibody. In some aspects, the cysteine residue is engineered into the antibody at position 239 (IgG1) as determined by the EU index (Kabat, Sequences of Proteins of Immunological Interest (National Institutes of Health, Bethesda, Md., 1987 and 1991).

C. Conjugation of Drug-Linkers to Antibodies

Antibody drug conjugates (ADCs) are formed by conjugation of a therapeutic antibody to a drug linker as described herein. The therapeutic antibody is selected by one of skill for its ability to bind specifically to a protein expressed on the external surface of a cancer cell. Preferably, the protein is differentially expressed on cancer cells, i.e., the protein is expressed at higher levels on cancer cells as compared to normal cells in the subject to be treated with the combination of an ADC and an FLT3 inhibitor.

Examples of therapeutic antibodies that can form the basis of an ADC include, e.g., anti-CD33 antibodies, such as h2H12 comprising heavy chain variable region SEQ ID NO:2 and light chain variable region SEQ ID NO: 1; anti-CD123 antibodies, such as h7G3 comprising heavy chain variable region SEQ ID NO:8 and light chain variable region SEQ ID NO:9; anti-CD19 antibodies, such as hBU12 comprising heavy chain variable region SEQ ID NO: 11 and light chain variable region SEQ ID NO: 10; and anti-CD70 antibodies, such as h1F6 comprising heavy chain variable region SEQ ID NO:13 and light chain variable region SEQ ID NO:12.

In some embodiments, the antibody of the ADC includes an antibody constant region with a mutation in the heavy chain to facilitate conjugation of a PBD molecule to the antibody. The constant region is a preferably a human IgG1 constant region. In some embodiments, the heavy chain constant region has a substitution mutation at amino acid 239 using the EU index according to Kabat, i.e., referred to herein as S239C. The cysteine residue at position 239 is the point of attachment for the PBD molecule. The structure of the antibody, the linker and the PBD molecule is shown in Formula 3. Methods to make the PBD conjugated ADCs are disclosed in PCT publication WO 2011/130613, which is incorporated by reference for all purposes.

II. FLT3 Inhibitors

The term "FLT3" as used herein refers to the FMS-like tyrosine kinase 3 protein (NCBI Reference Sequence: NP_004110.2). FLT3 is also known as CD135 or fetal liver kinase-2 (Flk2). FLT3 is a cytokine receptor which belongs to the receptor tyrosine kinase class III and is the receptor for the cytokine Flt3 ligand (FLT3L). FLT3 mutations are found in about 30% of acute myeloid leukemia (AML) patients. (Levis, M. *ASH Education Book* 2013:220-226 (2013)). FLT3 mutations fall into two general classes and can be identified by those of skill in the art. The first class is internal tandem duplications (FLT3/ITD mutations) in or near the juxtamembrane domain of the receptor. The second class includes point mutations resulting in single amino acid substitutions occurring within the activation loop of the tyrosine kinase domain (FLT3/TKD mutations). Ibid. Methods of identifying FLT3 mutations are known to those of skill in the art. See, e.g., Quentmeier et al., *Leukemia* 17:120-124 (2003).

The term "FLT3 inhibitor or inhibitors" as used herein refers to e.g., N-(2-diethylaminoethyl)-5-[(Z)-(5-fluoro-2-oxo-1H-indol-3-ylidene)methyl]-2,4-dimethyl-1H-pyrrole-3-carboxamide, sunitinib, also know as SU11248, and marketed as SUTENT (sunitinib malate); 4-[4-[[4-chloro-3-(trifluoromethyl)phenyl]carbamoylamino]phenoxy]-N-methyl-pyridine-2-carboxamide, sorafenib, also known as BAY 43-9006, marketed as NEXAVAR (sorafenib); (9S,10R,11R,13R)-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiamzonine-1-one, also know as midostaurin or PKC412; (5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one, also know as lestaurtinib or CEP-701; 1-(5-(tert-Butyl)isoxazol-3-yl)-3-(4-(7-(2-morpholinoethoxy)benzo[d]imidazo[2,1-b]thiazol-2-yl)phenyl)urea, also known as Quizartinib or AC220; 1-(2-{5-[(3-Methyloxetan-3-yl)methoxy]-1H-benzimidazol-1-yl}quinolin-8-yl)piperidin-4-amine, also known as Crenolanib or CP-868,596-26. See, e.g., Wander S. A., *Ther Adv Hematol.* 5: 65-77 (2014). Other FLT3 inhibitors include Pexidartinib (PLX-3397), Tap et al., *N Engl J Med*, 373:428-437 (2015); gilteritinib (ASP2215), Smith et al., *Blood:* 126 (23) (2015); FLX-925, also known as AMG-925, Li et al. *Mol. Cancer Ther.* 14: 375-83 (2015); and G-749, Lee et al., *Blood.* 123: 2209-2219 (2014).

III. Cancers that be Treated Using Combinations of PBD-ADCs and FLT3 Inhibitors

Cancers that can be treated using combinations of PBD-ADCs and FLT3 inhibitors are cancers that express antigens that are specifically bound by the antibody portion of the ADC. Examplary cancers are cancers that express cancer-specific antigens, e.g., CD33, CD123, CD19, and CD70.

CD33 positive cancers can be treated using a combination of a CD33-binding ADC and an FLT3 inhibitor. CD33-expressing cancers show detectable levels of CD33 measured at either the protein (e.g., by immunoassay using one of the exemplified antibodies) or mRNA level. Some such cancers show elevated levels of CD33 relative to noncancerous tissue of the same type, preferably from the same patient. An exemplary level of CD33 on cancer cells amenable to treatment is 5000-150000 CD33 molecules per cell, although higher or lower levels can be treated. Optionally, a level of CD33 in a cancer is measured before performing treatment.

For example, an ADC that includes an antibody that specifically binds to the human CD33 protein can be used in combination with an FLT3 inhibitor to treat a human subject who has a cancer that expresses that CD33 protein. Such cancers include, e.g., myeloid diseases such as, acute myeloid leukemia (AML), chronic myeloid leukemia (CML), other myeloproliferative disorders, including chronic myelomonocytic leukemia and chronic myeloproliferative disorders, acute promyelocytic leukemia (APL), thrombocytic leukemia, a myelodysplastic syndrome, precursor B-cell acute lymphoblastic leukemia (preB-ALL), precursor T-cell acute lymphoblastic leukemia (preT-ALL), multiple myeloma (MM), mast cell disease including mast cell leukemia and mast cell sarcoma, myeloid sarcomas, refractory anemia, a preleukemia syndrome, a lymphoid leukemia, or an undifferentiated leukemia. The treatment can also be applied to patients who are treatment naïve, who are refractory to conventional treatments (e.g., chemotherapy or MYLOTARG® (gemtuzumab ozogamicin), or who have relapsed following a response to such treatments.

A combination of a CD33-ADC and an FLT3 inhibitor can be used to treat cancers that express CD33 protein. In one embodiment, a subject with a CD33 expressing cancer is treated with a combination of an ADC comprising the h2H12 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with a CD33 expressing cancer is treated with a combination of an ADC comprising the h2H12 antibody conjugated to a PBD-drug linker of formula 3 and the FLT3 inhibitor selected from quizartinib, gilteritinib, or FLX-925, also known as AMG-925. The CD33 expressing cancer for treatment with a CD33-ADC and FLT3 inhibitor is selected from, e.g., CD33-positive acute myeloid leukemia (AML), CD33-positive chronic myeloid leukemia (CML), CD33-positive chronic myelomonocytic leukemia (CMML), CD33-positive thyroid leukemia, CD33-positive myelodysplastic syndrome, CD33-positive myeloproliferative disorder, CD33-positive refractory anemia, CD33-positive preleukemia syndrome, CD33-positive lymphoid leukemia, CD33-positive undifferentiated leukemia, CD33-positive precursor B-cell acute lymphoblastic leukemia (preB-ALL), CD33-positive precursor T-cell acute lymphoblastic leukemia (preT-ALL), CD33-positive multiple myeloma (MM) and CD33-positive mast cell disease including mast cell leukemia and mast cell sarcoma.

In one embodiment, a subject with CD33-positive acute myeloid leukemia (AML), is treated with a combination of an ADC comprising the h2H12 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with CD33-positive AML is treated with a combination of an ADC comprising the h2H12 antibody conjugated to a PBD-drug linker of formula 3 and the FLT3 inhibitor selected from quizartinib, gilteritinib, or FLX-925, also known as AMG-925.

In another embodiment, a subject with a CD33 expressing cancer is treated with a combination of an ADC comprising the h2H12 antibody conjugated to a PBD-drug linker of formula 3 and the FLT3 inhibitor quizartinib In another embodiment, a subject with a CD33 expressing cancer is treated with a combination of an ADC comprising the h2H12 antibody conjugated to a PBD-drug linker of formula 3 and the FLT3 inhibitor gilteritinib.

In another embodiment, a subject with a CD33 expressing cancer is treated with a combination of an ADC comprising the h2H12 antibody conjugated to a PBD-drug linker of formula 3 and the FLT3 inhibitor FLX-925, also known as AMG-925.

CD123 positive cancers can be treated using a combination of a CD123-binding ADC and an FLT3 inhibitor. CD123-expressing cancers show detectable levels of CD123 measured at either the protein (e.g., by immunoassay using one of the exemplified antibodies) or mRNA level. Some such cancers show elevated levels of CD123 relative to noncancerous tissue of the same type, preferably from the same patient. An exemplary level of CD123 on cancer cells amenable to treatment is 5000-150000 CD123 molecules per cell, although higher or lower levels can be treated. Optionally, a level of CD123 in a cancer is measured before performing treatment.

For example, an ADC that includes an antibody that specifically binds to the human CD123 protein can be used in combination with an FLT3 inhibitor to treat a human subject who has a cancer that expresses that CD123 protein. Such cancers include, e.g., myeloid diseases such as, acute myeloid leukemia (AML) and myelodysplastic syndrome (MDS). Other cancers include B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

A combination of a CD123-ADC and an FLT3 inhibitor can be used to treat cancers that express CD123 protein. In one embodiment, a subject with a CD123 positive cancer is treated with a combination of an ADC comprising the h7G3 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with a CD123 expressing cancer is treated with a combination of an ADC comprising the h7G3 antibody conjugated to a PBD-drug linker of formula 3 and an FLT3 inhibitor selected from quizartinib, gilteritinib, or FLX-925, also known as AMG-925. The CD123 expressing cancer for treatment with a CD123-ADC and an FLT3 inhibitor is selected from, e.g., acute myeloid leukemia (AML) and myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

In one embodiment, a subject with CD123-positive acute myeloid leukemia (AML), is treated with a combination of an ADC comprising the h7G3 antibody conjugated to a PBD-drug linker of formula 3 and an FLT3 inhibitor selected from midostaurin, quizartinib, crenolanib, gilteritinib, or G-749. In another embodiment, a subject with CD123-positive AML is treated with a combination of an ADC comprising the h7G3 antibody conjugated to a PBD-drug linker of formula 3 and the FLT3 inhibitor selected from quizartinib, gilteritinib, or FLX-925, also known as AMG-925.

In another embodiment, a subject with a CD123 expressing cancer is treated with a combination of an ADC comprising the h7G3 antibody conjugated to a PBD-drug linker of formula 3 and the FLT3 inhibitor quizartinib In another embodiment, a subject with a CD123 expressing cancer is treated with a combination of an ADC comprising the h7G3 antibody conjugated to a PBD-drug linker of formula 3 and the FLT3 inhibitor gilteritinib.

In another embodiment, a subject with a CD123 expressing cancer is treated with a combination of an ADC comprising the h7G3 antibody conjugated to a PBD-drug linker of formula 3 and the FLT3 inhibitor FLX-925, also known as AMG-925.

CD19 positive cancers can be treated using a combination of a CD19-binding ADC and an FLT3 inhibitor. CD19-expressing cancers show detectable levels of CD19 measured at either the protein (e.g., by immunoassay using one of the exemplified antibodies) or mRNA level. Some such cancers show elevated levels of CD19 relative to noncancerous tissue of the same type, preferably from the same patient. An exemplary level of CD19 on cancer cells amenable to treatment is 5000-150000 CD19 molecules per cell, although higher or lower levels can be treated. Optionally, a level of CD19 in a cancer is measured before performing treatment.

For example, an ADC that includes an antibody that specifically binds to the human CD19 protein can be used in combination with an FLT3 inhibitor to treat a human subject who has a cancer that expresses that CD19 protein. Such cancers include, e.g., B cell malignancies, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small non-cleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia; hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

A combination of a CD19-ADC and an FLT3 inhibitor can be used to treat cancers that express CD19 protein. In one embodiment, a subject with a CD19 positive cancer is treated with a combination of an ADC comprising the hBU12 antibody conjugated to a PBD-drug linker of formula 3 and an FLT3 inhibitor selected from midostaurin, quizartinib, crenolanib, gilteritinib, or G-749. In another embodiment, a subject with a CD19 expressing cancer is treated with a combination of an ADC comprising the hBU12 antibody conjugated to a PBD-drug linker of formula 3 and the FLT3 inhibitor selected from quizartinib, gilteritinib, or FLX-925, also known as AMG-925. The CD19 expressing cancer for treatment with a CD19-ADC and an FLT3 inhibitor is selected from, e.g., B cell malignancies, including, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small non-cleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia; hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

In one embodiment, a subject with CD19-positive non-hodgkins lymphoma (NHL) is treated with a combination of an ADC comprising the hBU12 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with CD19-positive NHL is treated with a combination of an ADC comprising the hBU12 antibody conjugated to a PBD-drug linker of formula 3 and an FLT3 inhibitor selected from quizartinib, gilteritinib, or FLX-925, also known as AMG-925.

In another embodiment, a subject with CD19-positive NHL is treated with a combination of an ADC comprising the hBU12 antibody conjugated to a PBD-drug linker of formula 3 and the FLT3 inhibitor quizartinib In another embodiment, a subject with CD19-positive NHL is treated with a combination of an ADC comprising the hBU12 antibody conjugated to a PBD-drug linker of formula 3 and the FLT3 inhibitor gilteritinib.

In another embodiment, a subject with CD19-positive NHL is treated with a combination of an ADC comprising the hBU12 antibody conjugated to a PBD-drug linker of formula 3 and the FLT3 inhibitor FLX-925, also known as AMG-925.

In one embodiment, a subject with CD19-positive acute lymphoblastic leukemia (ALL) is treated with a combination of an ADC comprising the hBU12 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with CD19-positive ALL is treated with a combination of an ADC comprising the hBU12 antibody conjugated to a PBD-drug linker of formula 3 and an FLT3 inhibitor selected from quizartinib, gilteritinib, or FLX-925, also known as AMG-925.

In another embodiment, a subject with CD19-positive ALL is treated with a combination of an ADC comprising the hBU12 antibody conjugated to a PBD-drug linker of formula 3 and the FLT3 inhibitor quizartinib In another embodiment, a subject with CD19-positive ALL is treated with a combination of an ADC comprising the hBU12 antibody conjugated to a PBD-drug linker of formula 3 and the FLT3 inhibitor gilteritinib.

In another embodiment, a subject with CD19-positive ALL is treated with a combination of an ADC comprising the hBU12 antibody conjugated to a PBD-drug linker of formula 3 and the FLT3 inhibitor FLX-925, also known as AMG-925.

In one embodiment, a subject with CD19-positive hodgkins lymphoma is treated with a combination of an ADC comprising the hBU12 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with CD19-positive hodgkins lymphoma is treated with a combination of an ADC comprising the hBU12 antibody conjugated to a PBD-drug linker of formula 3 and the FLT3 inhibitor selected from quizartinib, gilteritinib, or FLX-925, also known as AMG-925.

In another embodiment, a subject with CD19-positive hodgkins lymphoma is treated with a combination of an ADC comprising the hBU12 antibody conjugated to a PBD-drug linker of formula 3 and the FLT3 inhibitor quizartinib In another embodiment, a subject with CD19-positive hodgkins lymphoma is treated with a combination of an ADC comprising the hBU12 antibody conjugated to a PBD-drug linker of formula 3 and the FLT3 inhibitor gilteritinib.

In another embodiment, a subject with CD19-positive hodgkins lymphoma is treated with a combination of an ADC comprising the hBU12 antibody conjugated to a PBD-drug linker of formula 3 and the FLT3 inhibitor FLX-925, also known as AMG-925.

CD70 positive cancers can be treated using a combination of a CD70-binding ADC and an FLT3 inhibitor. CD70-expressing cancers show detectable levels of CD70 measured at either the protein (e.g., by immunoassay using one of the exemplified antibodies) or mRNA level. Some such cancers show elevated levels of CD70 relative to noncancerous tissue of the same type, preferably from the same patient. An exemplary level of CD70 on cancer cells amenable to treatment is 5000-150000 CD70 molecules per cell, although higher or lower levels can be treated. Optionally, a level of CD70 in a cancer is measured before performing treatment.

For example, an ADC that includes an antibody that specifically binds to the human CD70 protein can be used in combination with an FLT3 inhibitor to treat a human subject who has a cancer that expresses that CD70 protein. Such cancers include, Non-Hodgkin's Lymphoma (NHL), including NHL subtypes such as indolent NHLs, follicular NHLs, small lymphocytic lymphomas, lymphoplasmacytic NHLs, or marginal zone NHLs; Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

A combination of a CD70-ADC and an FLT3 inhibitor can be used to treat cancers that express CD70 protein. In one embodiment, a subject with a CD70 positive cancer is treated with a combination of an ADC comprising the h1F6 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with a CD70 expressing cancer is treated with a combination of an ADC comprising the h1F6 antibody conjugated to a PBD-drug linker of formula 3 and an FLT3 inhibitor selected from quizartinib, gilteritinib, or FLX-925, also known as AMG-925. The CD70 expressing cancer for treatment with a CD70-ADC and an FLT3 inhibitor is selected from, e.g., Non-Hodgkin's Lymphoma (NHL), including NHL subtypes such as indolent NHLs, follicular NHLs, small lymphocytic lymphomas, lymphoplasmacytic NHLs, or marginal zone NHLs; Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas.

In one embodiment, a subject with CD70-positive non-hodgkins lymphoma (NHL) is treated with a combination of an ADC comprising the h1F6 antibody conjugated to a PBD-drug linker of formula 3 and FLT3 inhibitor selected from midostaurin, quizartinib, crenolanib, gilteritinib, FLX-925, also known as AMG-925, or G-749. In another embodiment, a subject with CD70-positive NHL is treated with a combination of an ADC comprising the h1F6 antibody conjugated to a PBD-drug linker of formula 3 and an FLT3 inhibitor selected from quizartinib, gilteritinib, or FLX-925, also known as AMG-925.

In another embodiment, a subject with CD70-positive NHL is treated with a combination of an ADC comprising the h1F6 antibody conjugated to a PBD-drug linker of formula 3 and the FLT3 inhibitor quizartinib In another embodiment, a subject with CD70-positive NHL is treated with a combination of an ADC comprising the h1F6 antibody conjugated to a PBD-drug linker of formula 3 and the FLT3 inhibitor gilteritinib.

In another embodiment, a subject with CD70-positive NHL is treated with a combination of an ADC comprising the h1F6 antibody conjugated to a PBD-drug linker of formula 3 and the FLT3 inhibitor FLX-925, also known as AMG-925.

In one embodiment, a subject with CD70-positive renal cell carcinoma (RCC) is treated with a combination of an ADC comprising the h1F6 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with CD70-positive RCC is treated with a combination of an ADC comprising the h1F6 antibody conjugated to a PBD-drug linker of formula 3 and an FLT3 inhibitor selected from quizartinib, gilteritinib, or FLX-925, also known as AMG-925.

In another embodiment, a subject with CD70-positive RCC is treated with a combination of an ADC comprising the h1F6 antibody conjugated to a PBD-drug linker of formula 3 and the FLT3 inhibitor quizartinib In another embodiment, a subject with CD70-positive RCC is treated with a combination of an ADC comprising the h1F6 antibody conjugated to a PBD-drug linker of formula 3 and the FLT3 inhibitor gilteritinib.

In another embodiment, a subject with CD70-positive RCC is treated with a combination of an ADC comprising the h1F6 antibody conjugated to a PBD-drug linker of formula 3 and the FLT3 inhibitor FLX-925, also known as AMG-925.

CD352 positive cancers can be treated using a combination of a CD352-binding ADC and an FLT3 inhibitor. CD352-expressing cancers show detectable levels of CD352 measured at either the protein (e.g., by immunoassay using one of the exemplified antibodies) or mRNA level. Some such cancers show elevated levels of CD352 relative to noncancerous tissue of the same type, preferably from the same patient. An exemplary level of CD352 on cancer cells amenable to treatment is 5000-150000 CD352 molecules per cell, although higher or lower levels can be treated. Optionally, a level of CD352 in a cancer is measured before performing treatment.

For example, an ADC that includes an antibody that specifically binds to the human CD352 protein can be used in combination with an FLT3 inhibitor to treat a human subject who has a cancer that expresses that CD352 protein. Such cancers include, e.g., hematological malignancies, including B-cell, T-cell, and NK-cell malignancies. In some methods of treatment, the patient has a cancer, which is a multiple myeloma (MM), an acute myeloid leukemia (AML), a chronic lymphocytic leukemia (CLL), a T-Cell or B-cell lymphoma such as, e.g., a non-Hodgkin's lymphoma (NHL), or myeloma related malignacies such as primary amyloidosis, Waldenström's macroglobulinemia, or high risk MGUS (monoclonal gammopathy of undetermined significance).

A combination of a CD352-ADC and an FLT3 inhibitor can be used to treat cancers that express CD352 protein. In one embodiment, a subject with a CD352 positive cancer is treated with a combination of an ADC comprising the h20F3 antibody conjugated to a PBD-drug linker of formula 3 and an FLT3 inhibitor selected from midostaurin, quizartinib, crenolanib, gilteritinib, FLX-925, also known as AMG-925, or G-749. In another embodiment, a subject with a CD352 expressing cancer is treated with a combination of an ADC comprising the h20F3 antibody conjugated to a PBD-drug linker of formula 3 and an FLT3 inhibitor selected from quizartinib, gilteritinib, or FLX-925, also known as AMG-925. The CD352 expressing cancer for treatment with a CD352-ADC and an FLT3 inhibitor is selected from, e.g., multiple myeloma (MM), an acute myeloid leukemia (AML), a chronic lymphocytic leukemia (CLL), a T-Cell or B-cell lymphoma such as, e.g., a non-Hodgkin's lymphoma (NHL), or myeloma related malignacies such as primary amyloidosis, Waldenström's macroglobulinemia, or high risk MGUS (monoclonal gammopathy of undetermined significance).

In one embodiment, a subject with CD352-positive multiple myeloma (MM), is treated with a combination of an ADC comprising the h20F3 antibody conjugated to a PBD-drug linker of formula 3 and an FLT3 inhibitor selected from midostaurin, quizartinib, crenolanib, gilteritinib, or G-749. In another embodiment, a subject with CD352-positive MM is treated with a combination of an ADC comprising the h20F3 antibody conjugated to a PBD-drug linker of formula 3 and the FLT3 inhibitor selected from quizartinib, gilteritinib, or FLX-925, also known as AMG-925.

In another embodiment, a subject with a CD352 expressing cancer is treated with a combination of an ADC comprising the h20F3 antibody conjugated to a PBD-drug linker of formula 3 and the FLT3 inhibitor quizartinib.

In another embodiment, a subject with a CD352 expressing cancer is treated with a combination of an ADC comprising the h20F3 antibody conjugated to a PBD-drug linker of formula 3 and the FLT3 inhibitor gilteritinib.

In another embodiment, a subject with a CD352 expressing cancer is treated with a combination of an ADC comprising the h20F3 antibody conjugated to a PBD-drug linker of formula 3 and the FLT3 inhibitor FLX-925, also known as AMG-925.

IV. Dosage and Administration

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. Formulations for ADCs comprising antibodies and a PBD molecules are disclosed e.g., at PCT/US2014/024466.

The ADC is administered intravenously. FLT3 inhibitors are administered in an appropriate manner as directed by the manufacturer. For example, FLT3 inhibitors can be administered orally.

An ADC comprising an antibody that specifically binds a protein expressed by a cancer can be combined with an FLT3 inhibitor concurrently or sequentially for treatment of a cancer or disorder, at the discretion of the treating physician.

The ADC can be administered in combination with a FLT3 inhibitor in the following dose ranges: 5-60 µg/kg, 5-40 µg/kg, 5-25 µg/kg, 10-30 µg/kg, 5-20 µg/kg, 5-15 µg/kg, or 5-10 µg/kg. In some embodiments the ADC is administered with an FLT3 inhibitor in a range from 10-40 µg/kg. In some embodiments, the ADC is administered at about 10 µg/kg in combination with FLT3 inhibitor. In another embodiment, the ADC is administered at 10 µg/kg in combination with an FLT3 inhibitor. In other embodiments, the ADC is administered at 5 µg/kg, 6 µg/kg, 7 µg/kg, 8 µg/kg, 9 µg/kg, 10 µg/kg, 15 µg/kg, 20 µg/kg, 25 µg/kg, 30 µg/kg, or 40 µg/kg in combination with an FLT3 inhibitor.

FLT3 inhibitors are adminstered in the following dosage ranges: 10-200 mg/m$^2$, 25-150 mg/m$^2$, or 50-100 mg/m$^2$. In some embodiments, FLT3 inhibitors are administered as a flat dose in combination with an ADC comprising a PBD molecule. For example, an FLT3 can be administered at ranges of 10-800 mg/day. An exemplary dose of gilternitinib is 120 mg daily. An exemplary dose range of Quazartinib is 30-60 mg daily.

In one embodiment, an ADC comprising an antibody that specifically binds a CD33 protein expressed by a cancer cell can be combined with an FLT3 inhibitor for treatment of a CD33-positive cancer. In a further embodiment, the ADC comprises the h2H12 antibody and is conjugated to a PBD molecule as shown in Formula 3. The h2H12 antibody comprises S239C mutations in the heavy chain constant region and the S239C residues are used for conjugation of the PBD molecule to the antibody.

The CD33-specific ADC, i.e., an ADC comprising the h2H12 antibody conjugated to a PBD molecule as in Formula 3, can be administered in combination with an FLT3 inhibitor in the following dose ranges: 5-60 µg/kg, 5-40 µg/kg, 5-25 µg/kg, 10-30 µg/kg, 5-20 µg/kg, 5-15 µg/kg, or 5-10 µg/kg. In some embodiments, the CD33-specific ADC, i.e., an ADC comprising the h2H12 antibody conjugated to a PBD molecule as in Formula 3, can be administered in combination with an FLT3 inhibitor in the in a range from 10-40 µg/kg. In some embodiments, the CD33-specific ADC is administered at about 10 µg/kg in combination with an FLT3 inhibitor. In another embodiment, the CD33-specific ADC is administered at 10 µg/kg in combination with an FLT3 inhibitor. In other embodiments, the CD33-specific ADC is administered at 5 µg/kg, 6 µg/kg, 7 µg/kg, 8 µg/kg, 9 µg/kg, 10 µg/kg, 15 µg/kg, 20 µg/kg, 25 µg/kg, 30 µg/kg or 40 µg/kg in combination with an FLT3 inhibitor.

The tumor of a patient can be assessed for FLT3 status before treatment begins. Patient tumors can be classified as FLT3 mutant or FLT3 wildtype. FLT3 mutations fall into two general classes and can be identified by those of skill in the art. The first class is internal tandem duplications (FLT3/ITD mutations) in or near the juxtamembrane domain of the receptor. The second class includes point mutations resulting in single amino acid substitutions occurring within the activation loop of the tyrosine kinase domain (FLT3/TKD mutations). (Levis, M. *ASH Education Book* 2013:220-226 (2013)).

In some embodiments, patients with FLT3 mutant tumors are administered a combination of a PBD-ADC and an FLT3 inhibitor.

A combination of a CD33-ADC and an FLT3 inhibitor can be used to treat cancers that express CD33 protein and that are classified as FLT3 mutant tumors. In one embodiment, a subject with a CD33-expressing cancer, which is also an FLT3 mutant cancer, is treated with a combination of an ADC comprising the h2H12 antibody conjugated to a PBD-drug linker of formula 3 and an FLT3 inhibitor selected from midostaurin, quizartinib, crenolanib, gilteritinib, or G-749. In another embodiment, a subject with a CD33-expressing cancer, which is FLT3 mutant, is treated with a combination of an ADC comprising the h2H12 antibody conjugated to a PBD-drug linker of formula 3 and an FLT3 inhibitor quizartinib, gilteritinib, or FLX-925, also known as AMG-925. The CD33-expressing cancer, which expresses an FLT3 mutation, for treatment with a CD33-ADC and FLT3 inhibitor is selected from, e.g., CD33-positive acute myeloid leukemia (AML), CD33-positive chronic myeloid leukemia (CML), CD33-positive chronic myelomonocytic leukemia (CMML), CD33-positive thyroid leukemia, CD33-positive myelodysplastic syndrome, CD33-positive myeloproliferative disorder, CD33-positive refractory anemia, CD33-positive preleukemia syndrome, CD33-positive lymphoid leukemia, CD33-positive undifferentiated leukemia, CD33-positive precursor B-cell acute lymphoblastic leukemia (preB-ALL), CD33-positive precursor T-cell acute lymphoblastic leukemia (preT-ALL), CD33-positive multiple myeloma (MM) and CD33-positive mast cell disease including mast cell leukemia and mast cell sarcoma. In a further embodiment, CD33 positive AML cells from a patient are classified as having an FLT3 mutation, and the patient is treated with a combination of an ADC comprising the h2H12 antibody conjugated to a PBD-drug linker of formula 3 and an FLT3 inhibitor selected from midostaurin, quizartinib, crenolanib, gilteritinib, or G-749.

A combination of a CD123-ADC and an FLT3 inhibitor can be used to treat cancers that express CD33 protein and that are classified as FLT3 mutant tumors. In one embodiment, a subject with a CD123 positive cancer, which is classified as having an FLT3 mutation, is treated with a combination of an ADC comprising the h7G3 antibody conjugated to a PBD-drug linker of formula 3 and an FLT3 inhibitor selected from midostaurin, quizartinib, crenolanib, gilteritinib, G-749, or FLX-925, also known as AMG-925. The CD123-expressing cancer having an FLT3 mutation for treatment with a CD123-ADC and an FLT3 inhibitor is selected from, e.g., acute myeloid leukemia (AML) and myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma. In a further embodiment, CD123 positive AML cells from a patient are classified as having an FLT3 mutation, and the patient is treated with a combination of an ADC comprising the h7G3 antibody conjugated to a PBD-drug linker of formula 3 and an FLT3 inhibitor selected from midostaurin, quizartinib, crenolanib, gilteritinib, G-749, or FLX-925, also known as AMG-925.

EXAMPLES

The following examples are offered to illustrate, but not to limit the claimed invention.

Example 1: ADC's Comprising PBDs Exhibit Synergism in Combination with FLT3 Inhibitors Methods
In Vitro Cytotoxicity Assay Cell Lines: The following cell lines were cultured in the vendor recommended conditions. KG-1 (ATCC, CCL-246), KG-1(8031) (ATCC, CRL-8031), MV-4-11 (ATCC, CRL-9591), TF1a (ATCC, CRL-2451), THP-1 (ATCC, TIB-202), Kasumi-1 (DSMZ, ACC-220), ME-1 (DSMZ, ACC-537), and MOLM-13 (DSMZ, ACC-554).

Small molecules: gilteritinib/ASP2215, crenolanib, G-749, midostaurin/PKC412, and quizartinib/AC220 were purchased from Selleck Chemicals (Houston, Tex., USA). Compounds were resuspended in DMSO and stocks were stored at −80° C. Isobologram assay: 1000 cells/well were plated in 384-well plates (BD Falcon Cat#353988). Cells were treated with all pairwise combinations of 19 doses of ASP2215, crenolanib, G-749, midostaurin, and quizartinib consisting of 2-fold dilutions starting at 10 uM and 11 doses of SGN-CD33A or SGN-CD123 consisting of 3-fold dilutions starting at 1 ug/mL. Cells were then incubated for 96 hours at 37° C. in 5% CO2. Cell viability was assessed by adding CellTiter-Glo® (Promega, WI, USA) and measuring luminescence with an Envision® Multilabel Reader (Perkin Elmer, MA, USA).

Drug Combination Computational Analysis
Data Organization and Normalization:

For the purpose of downstream analyses, CellTiter-Glo luminescence values are converted to viability percentages as follows. Luminescence values are arranged in a matrix with the i,jth entry, $V(i,j)$, $i=1, \ldots, N$, $j=1, \ldots, M$, representing cell viability after treating with Drug 1 at concentration i and Drug 2 at concentration j. Concentrations are assumed to increase with i and j, with $i=1$ corresponding to no treatment with Drug 1, and $j=1$ corresponding to no treatment with Drug 2. Different normalization schemes are possible, but for this analysis we simply divide the matrix of luminescence values by the $V(1,1)$ entry, which corresponds to no treatment with either drug. Normalization is performed at an individual replicate level. Additivity Models: In the realm of drug combination studies, the concepts of synergy and antagonism refer to cooperative or non-cooperative deviations from models of additivity, which under various assumptions reflect a null expectation of the effect of combining two agents on cell viability. Additivity models predict the combined effect given the separate single-agent effects. That is, given a combination dose (i0, j0) an additivity model W(i0,j0) predicts V(i0,j0) from {V(1,j), j=1, ... M} and {V(i,1), i=1, ... N}, under the null expectation. Commonly used additivity models include Bliss, Loewe and Highest Single Agent (HSA) [1,2,3]. The Loewe model requires continuous and monotone single-agent data, for which we use a Hill equation, $$F(x) = (U_\infty - U_0)\left(\frac{x^H}{x^H + Ec50^H}\right) + U_0$$

where $U_\infty$, $U_0$, H, and Ec50 are fitted parameters. A Hill equation is fit to each single-agent dataset: F1(x) is fit to {V(i,1)}, and F2(x) is fit to {V(1,j)}. Parameter fitting is performed using the method of non-linear least squares, as implemented in the R function nls( ). Bliss and HSA models can be calculated using either fitted or non-fitted single-agent data. In case multiple replicates are available at each dose, the Hill equations are fit simultaneously to all data points. In models using non-fitted data, the median observation at each single-agent dose is used to compute the model. Statistical determination of synergy/antagonism: Given an additivity model W(i,j) and observed data V(i,j), the dose combination (i,j) is deemed to be synergistic if V(i,j)<W(i,j) (greater cytotoxicity than predicted under the combined treatment), and antagonistic if V(i,j)>W(i,j). If multiple replicates V(i,j,k), k=1, ... K, exist for each V(i,j), one-sided t-tests can be used to assign a p-value to test the specific combination (i,j) for synergy ({V(i,j,k)−W(i,j)<0, k=1, ... K}) or antagonism ({V(i,j,k)−W(i,j)>0, k=1, ... K}). In testing all possible M*N dose combinations, we adjust for multiple testing using a Bonferroni correction. To further adjust for the potential occurrence of outlier measurements, and to highlight the assumption that if a dose combination (i,j) is truly synergistic, then neighboring dose combinations are likely to be synergistic, we introduce the concept of combination block tests. In this case, for a fixed combination (i0,j0), we consider the 3×3 block of nine combinations {V(i0+i,j0+j); i=0, 1, 2; j=0, 1, 2}, and ask if they collectively trend greater or less than the model predictions {W(i0+i, j0+j); i=0, 1, 2; j=0, 1, 2}. This translates in a straightforward way to a combination block t-test for synergy by testing {V(i0+i,j0+j)−W(i0+i,j0+j)<0; i=0, 1, 2; j=0, 1, 2}; or in the case of multiple replicates, {V(i0+i,j0+j,k)−W(i0+i,j0+j)<0; i=0, 1, 2; j=0, 1, 2; k=1, ... K}. The block t-test for antagonism uses the reverse inequality. We test over all 3×3 blocks, and adjust the p-values accordingly using a Bonferroni correction. Synergy metrics: best dose combinations and PTCDS: A number of synergy metrics are considered, in turn emphasizing strongly synergistic individual dose combinations or synergy across a range of combinations. Best dose combination: For a given experiment, the "best dose" combination is defined by scanning all 3×3 combination blocks that are tested as significantly synergistic at p<0.01, using the combination block test described above, for the single dose combination (i0,j0) that gives the greatest absolute positive difference W(i0,j0)−V(i0,j0) between the additive model and the observed data. The metric recorded is this difference. In the case of multiple replicates we use the median of the observations, $\hat{V}$(i0,j0) =median{V(i0,j0, k), k=1, ... K}, to represent the observed data at a fixed combination. Number of synergistic combination blocks: This is simply the number of (possibly overlapping) 3×3 dose combination blocks that tested as significantly synergistic at p<0.01 using the combination block test described above. Percent Total Cytotoxicity Due to Synergy (PTCDS): The cytotoxicity achieved at dose combination (i,j) is simply the value 100−V(i,j) (more generally, we replace 100 by the maximum value of the additivity model $W_m$=max{W(i,j), i=1, ... N, j=1, ... , M}). The total cytotoxicity observed across all dose combinations can therefore be defined as $$TC = \Sigma\{W_m - V(i,j), i=1, \ldots, N, j=1, \ldots, M\}.$$

On the other hand, $$TS = \Sigma\{W(i,j) - V(i,j), i=1, \ldots, N, j=1, \ldots, M\}$$

can be interpreted as the total synergy observed across all dose combinations, and TS/TC can be interpreted as the proportion of total cytotoxicity due to synergy. We define the Percent of Total Cytotoxicity Due to Synergy (PTCDS) as PTCDS=100*TS/TC. In the presence of multiple replicates, V(i,j) is replaced in the above definitions by the median observation $\hat{V}$(i,j).

1. M. C. Berenbaum, What is synergy?, Pharmacol Rev, 41 (1989), pp. 93-141
2. S. Loewe, The problem of synergism and antagonism of combined drugs, Arzneimittelforschung, 3 (1953, pp. 285-290.
3. C. I. Bliss, The toxicity of poisons applied jointly, Ann Appl Bio, 26 (19391, pp. 585-615.

Results

In Vitro Anti-Tumor Activity of CD33-ADC or CD123 ADC in Combination with FLT3 Inhibitors The cytotoxic activity of the CD33-ADC (h2H12EC antibody conjugated to SGD-1910, the pyrrolobenzodiazepine dimer drug-linker) was evaluated alone and in combination with hypomethylating agents or FLT3 inhibitors in several AML cell lines. The data is shown in FIG. 4. As shown in FIG. 1A, there was significant synergism in the cytotoxic activity of the ADC when combined with either 5-azacytidine (vidaza) or 5-aza-2-deoxycytidine (decitabine). However, the synergism exhibited by the combination of the CD33-ADC in combination with either the assessed FLT3 inhibitors was even more striking.

The cytotoxic activity of the CD123-ADC (h7G3EC antibody conjugated to SGD-1910, the pyrrolobenzodiazepine dimer drug-linker) was evaluated alone and in combination with hypomethylating agents or FLT3 inhibitors in several AML cell lines. As shown in FIG. 1A, there was significant synergism in the cytotoxic activity of the ADC when combined with either 5-azacytidine (vidaza) or 5-aza-2-deoxycytidine (decitabine). However, the synergism exhibited by the combination of the CD123-ADC in combination with the assessed FLT3 inhibitors was even more striking.

Figure 1B:
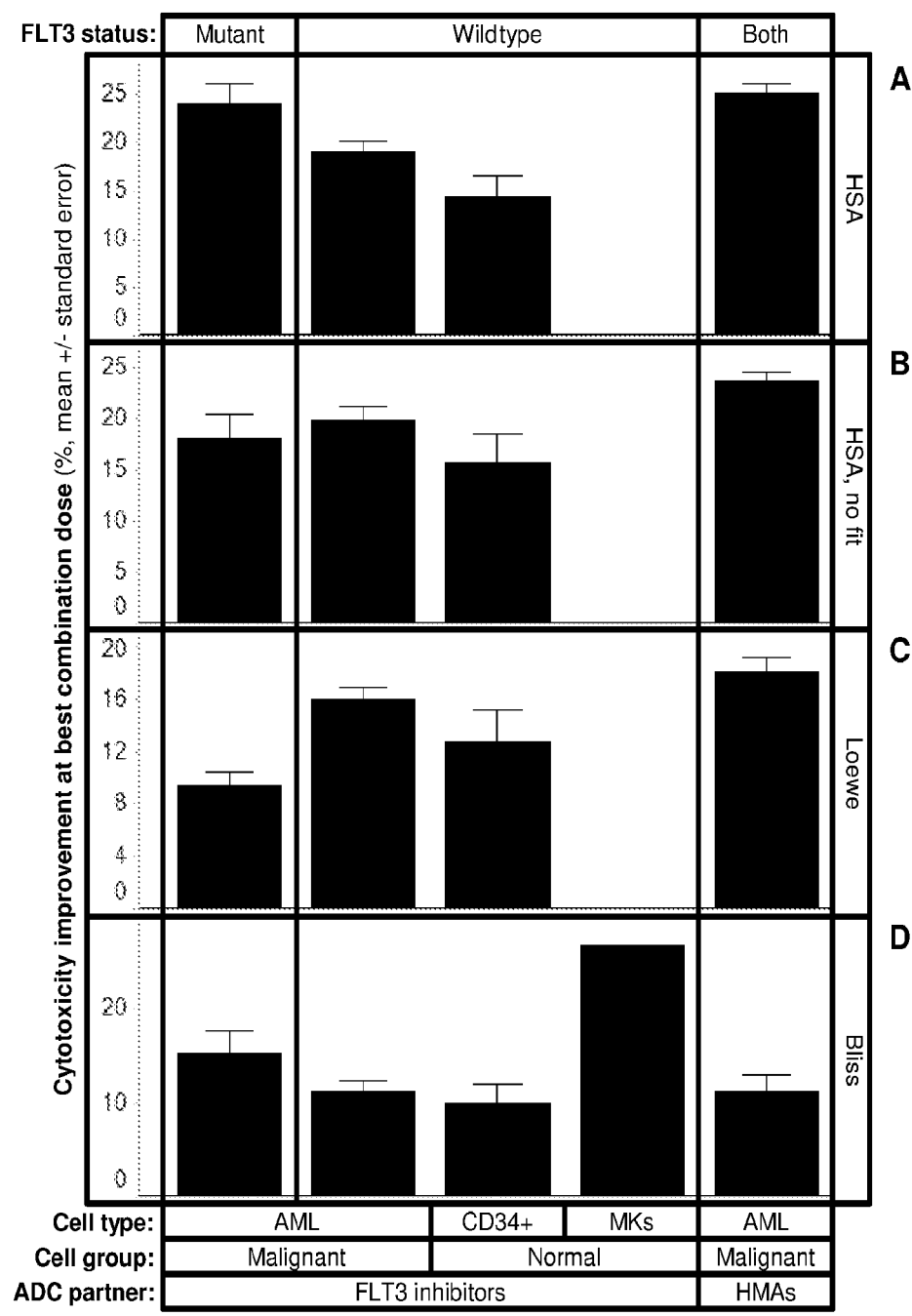

Thus, the cytotoxicity improvement is similar for PBD-ADCs combined with FLT3 inhibitors or with HMAs (FIG. 1B). In FIG. 1A, the cytotoxicity improvement (%) for the best combination dose ((viability, model, %)−(viability, observed, %)) is represented by deviation from the thick black bar. Individual combination-cell line pairs that like lie below the thick diagonal bar show improved cytotoxicity relative the expected viability according to the Loewe Additivity model of drug cooperation.

Figure 2A:
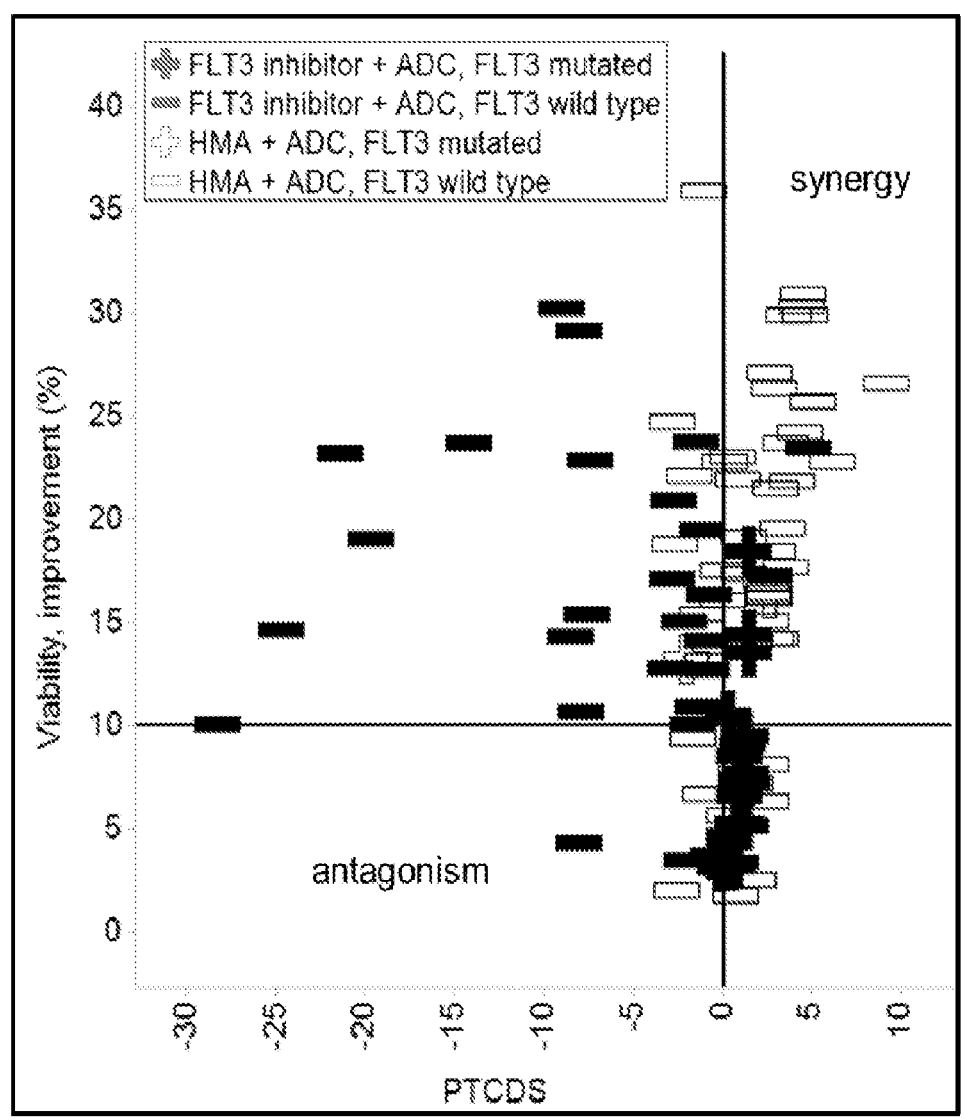
FIGS. 2A and 2B provide percent of total toxicity due to synergy (PTCDS) values for PBD-ADC combinations with FLT3 inhibitors in FLT3 mutant cell lines and FLT3 wild-type cell lines.
Figure 2B:
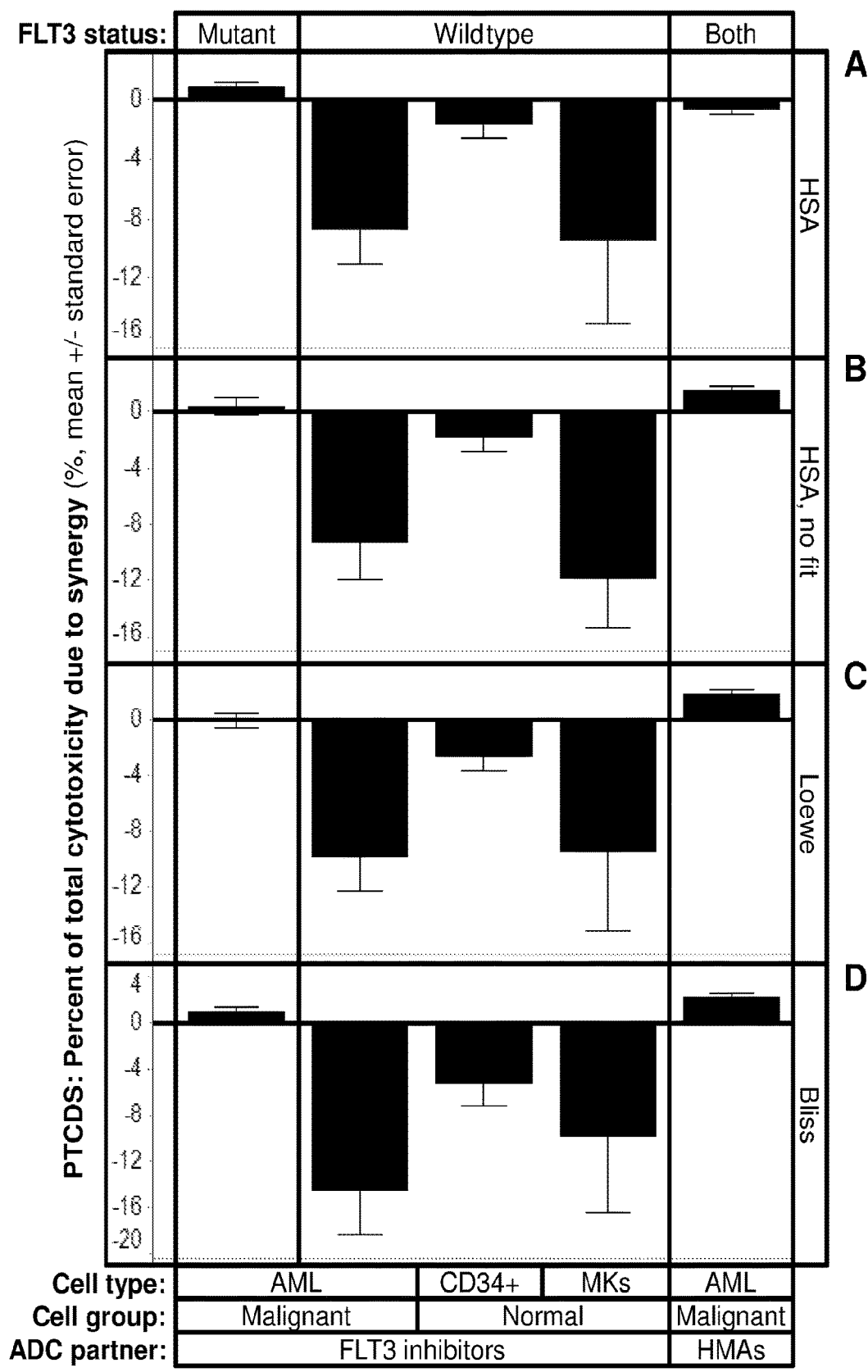

FIGS. 2A and 2B provide examples of cytotoxic activity for the combination of PBD-ADCs and FLT3 inhibitors in FLT3 wildtype or FLT3 mutant cells lines. FLT3 mutant cell lines included MOLM013 and MV4-11. FLT3 wildtype cell lines included Kasumi-1, TF1-α, KG-1_8031, KG-1_cb, ME-1, and THP-1. See, e.g., Quentmeier et al., Leukemia 17:120-124 (2003). Percent Total Cytotoxicity Due to Synergy (PTCDS) was assessed. Shown in FIG. 2A is a scatter plot of cytotoxicity improvement ((viability, model, %)-(viability, observed, %)) for the best combination dose (Viability, improvement (%))) on the y-axis versus the PTCDS (percent of total toxicity due to synergy, %) on the y-axis. Combination-cell line pairs with data points above and to the left of the horizontal and vertical black lines, respectively, have values for both metrics greater than expected by the Loewe Additivity model of drug cooperation, indicating synergy. PCTDS values for PBD-ADCs combined with FLT3 inhibitors in FLT3 mutant cell lines were similar to PTCDS values for PBD-ADCs combined with HMAs. Values in FLT3 mutant cell lines were generally greater than zero, indicating synergy or additivity. In contrast, PTCDS values For PBD-ADCs combined with FLT3 inhibitors in FLT3 wild type cell lines were generally negative, indicating antagonism or additivity.

Figure 3A:
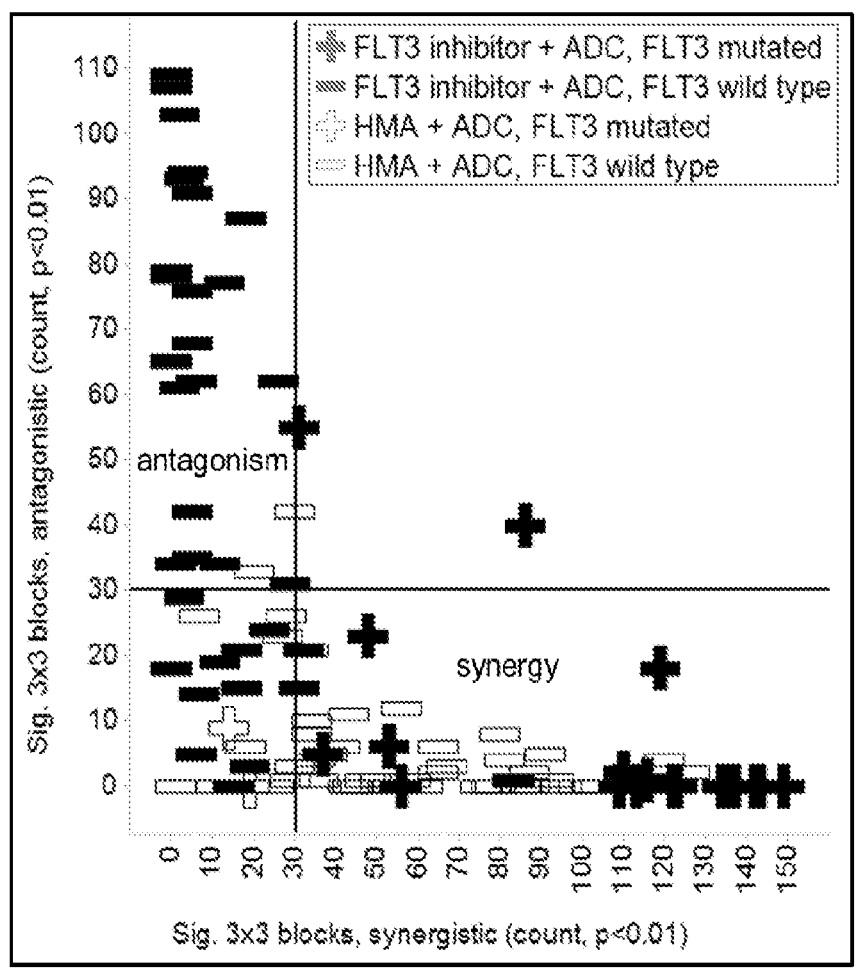
FIGS. 3A-3D show that PBD-ADC combinations with FLT3 inhibitors in FLT3 mutant cell lines have more synergistic and fewer antagonistic 3×3 dose blocks than FLT3 wildtype cell lines.
Figure 3B:
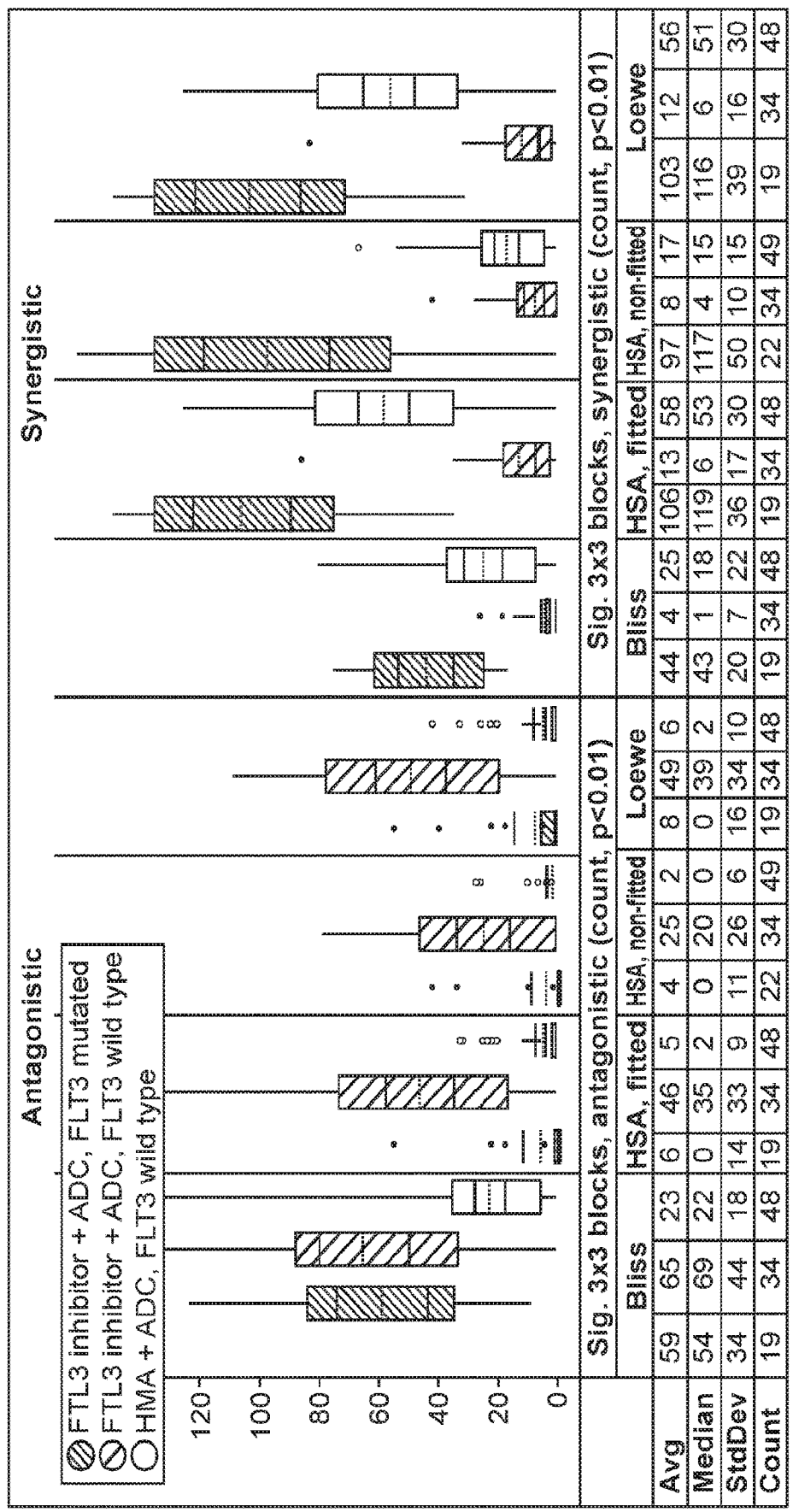
Figure 3C:
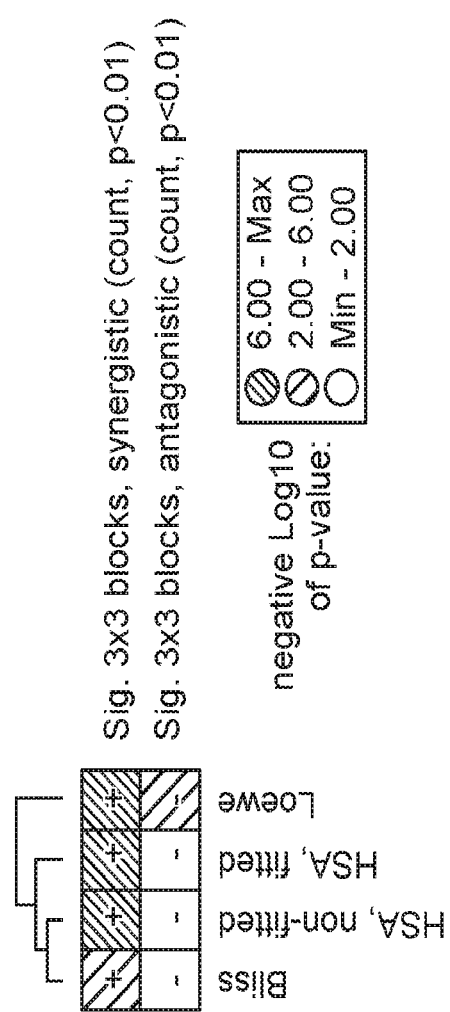
Figure 3D:
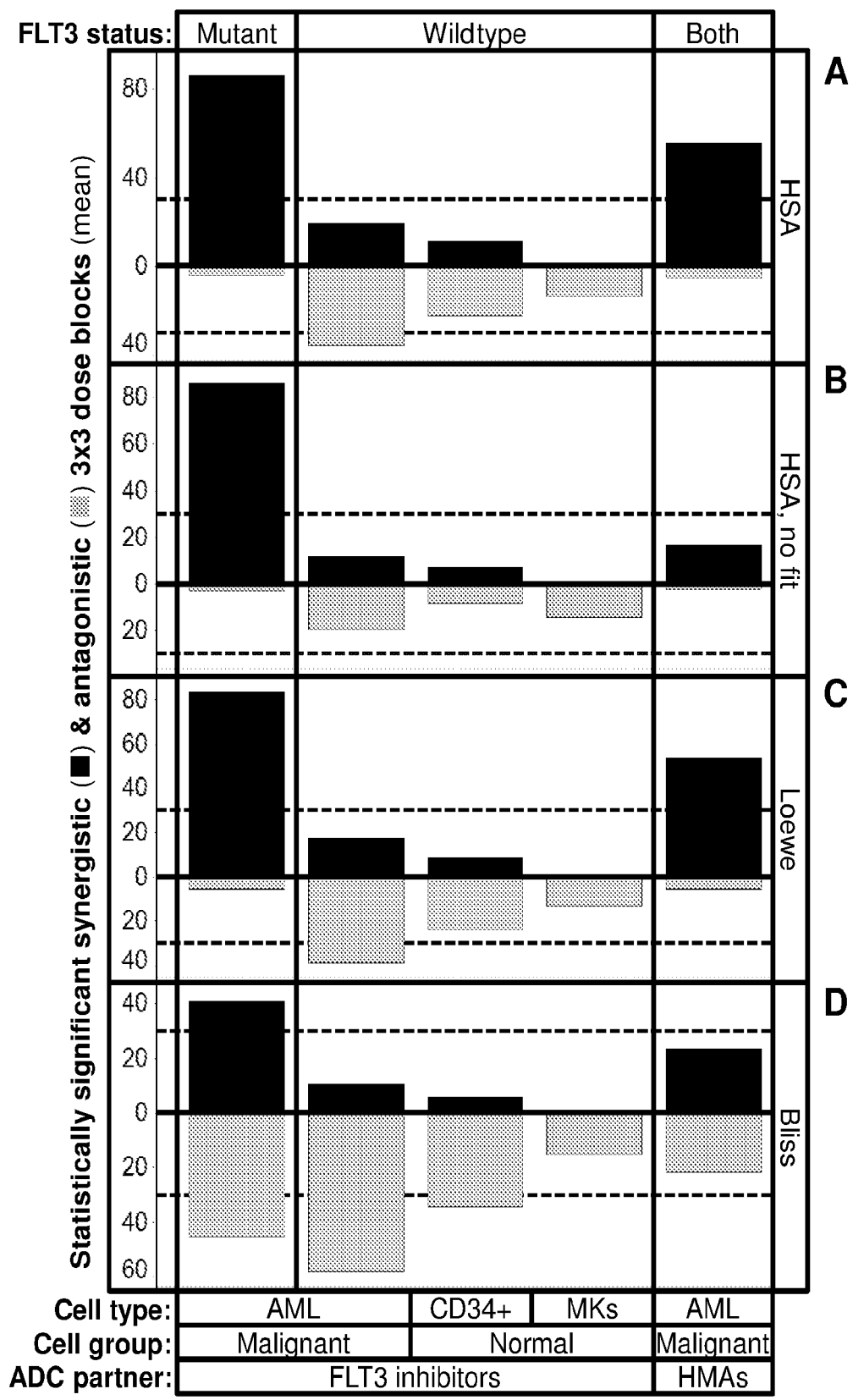

Cytotoxicity results from PBD-ADCs combined with FLT3 inhibitors in FLT3 mutant and wildtype cell lines were assessed for statistical significance using 3×3 dose blocks. Results are shown in FIGS. 3A-3D. FIG. 3A provides a comparison of the count of antagonistic (y-axis) and synergistic (x-axis) 3×3 dose blocks with p-values less than 0.01 according to the Loewe additivity model. Each data point represents a unique combination-cell line pair. FIG. 3B provides box plots of antagonistic and synergistic count of 3×3 dose blocks for each combination-FLT3 status group according to the Loewe Additivity model. FIG. 3C provides p-Values of comparisons between FLT3 wild type and FLT3 mutant cell lines for treatment with PBD ADCs in combination with FLT3 inhibitors. Gray (p<0.01, negative Log 10 p-value <2.00) and black (p<0.000001, negative Log 10 value >6.00) indicates statistical significance, whereas white indicates p-values >0.01 and negative Log 10 p-values of <2.00. Plus (+) and minus (−) symbols indicate that mean count of significant 3×3 dose blocks for FLT3 mutant cell lines is greater than or less than, respectively, that of FLT3 wild type cell lines. PBD-ADCs combined with FLT3 inhibitors in FLT3 mutant cell lines have more synergistic and fewer antagonistic 3×3 dose blocks that are statistically significant relative to FLT3 wild type cell lines.

The results demonstrate that PTCDS and cytotoxicity improvement at the best combination dose are similar for: PBD-ADCs combined with FLT3 inhibitors in FLT3 mutant cell lines; and PBD-ADCs combined with HMAs (synergistic combination, validated using in vitro and in vivo xenograft models) in a manner independent of FLT3 status. The count of synergistic and significant 3×3 dose blocks for PBD-ADCs combined with FLT3 inhibitors was significantly greater for FLT3 mutant cell lines compared to FLT3 wild type cell lines The observed synergy of PBD-ADCs combined with FLT3 inhibitors was widespread across the dose range tested, different FLT3 inhibitors tested, and different drug cooperation metrics. That is the synergy was independent of drug cooperation model (Bliss, HSA (raw or no-fit), and Loewe Additivity)

Figure 5:
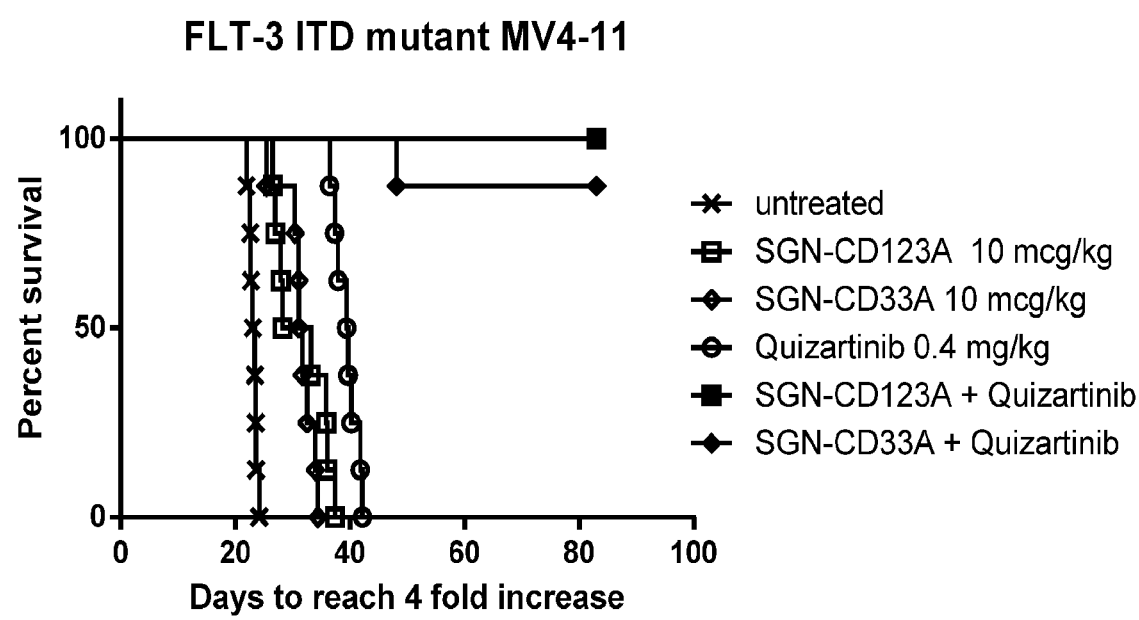
FIG. 5 shows a survival plot of FLT3/ITD MV4-11 xenografts after treatment with quizartinib, SGN-CD33A, SGN-CD123A, or a combination.

In Vivo Anti-Tumor Activity of CD33-ADC or CD123 ADC in Combination with FLT3 Inhibitors FIG. 5 shows the survival rates of FLT3/ITD mutant MV4-11 mice treated with different agents. Five million MV4-11 cells were implanted subcutaneously in SCID mice. Tumor growth was monitored throughout the course of the study with bilateral vernier caliper measurements, and mean tumor volumes were calculated using the equation (0.5× [length×width$^2$]). When tumors reached approximately 100 mm$^3$, this marked day 1 of dosing and mice were randomly assigned into groups of 8 mice to receive quizartinib, SGN-CD123A, SGN-CD33A, or quizartinib in combination with SGN-CD33A or SGN-CD123A.

As shown in FIG. 5, the survival plot of FLT3/ITD MV4-11 xenografts (tumor cells were implanted subcutaneously in SCID mice) shows percent survival after quizartinib treatment (0.4 mg/kg given daily for 21 days by mouth), SGN-CD33A (10 mcg/kg once by intraperitoneal injection), SGN-CD123A (10 mcg/kg once by intraperitoneal injection), or quizartinib combined with either SGN-CD33A or SGN-CD123A (n=8 in each group, p<0.001 by two-way ANOVA test). While the quizartinib, SGN-CD33A, and SGN-CD123A each induced delay of progression, the combination-treated animals remained alive by the end of the study. The median survival time for these mice was 23 days (untreated), 40 days (quizartinib), 31 days (SGN-CD33A), 31 days (SGN-CD123A), and not reached (combination quizartinib and either SGN-CD33A or SGN-CD123A). Mice with advanced tumor burden were sacrificed upon reaching tumor volumes of greater than 400 mm$^3$ or showing symptoms of hind limb paralysis, cranial swelling, and/or moribundity.

Figure 6:
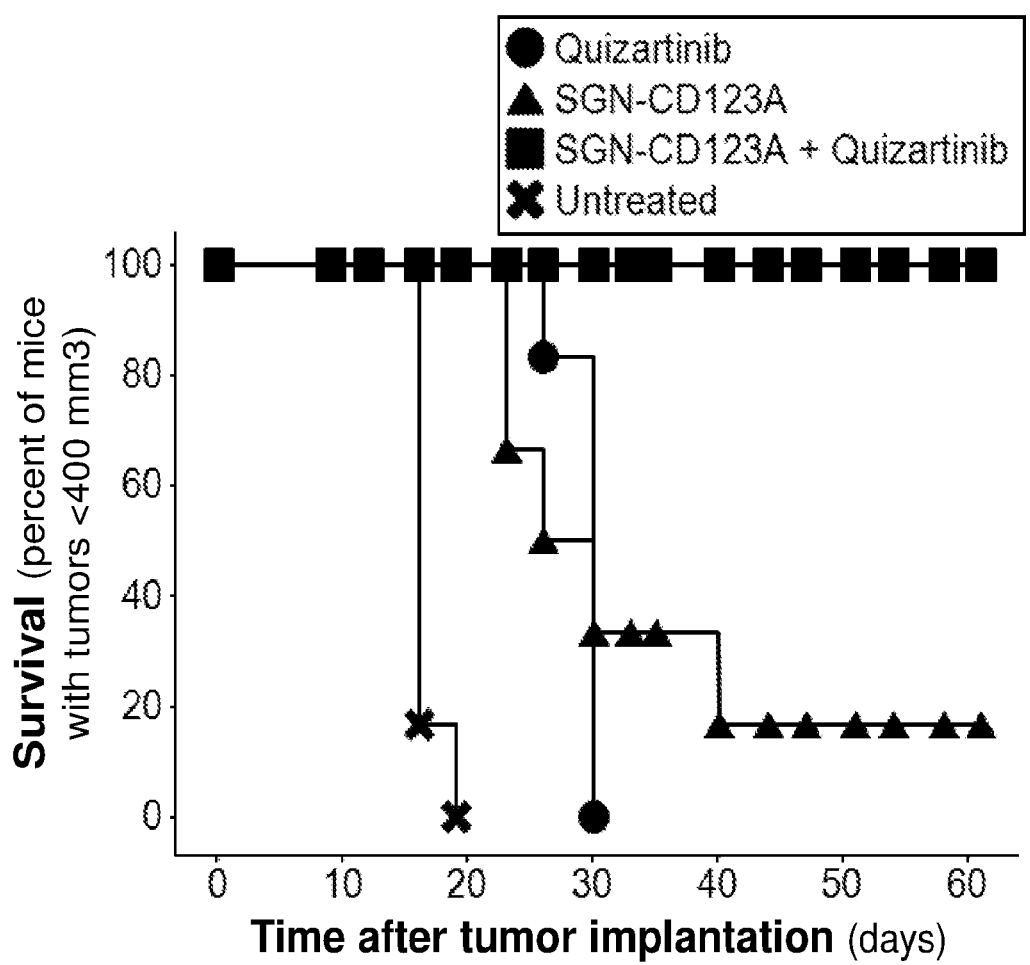
FIG. 6 shows a survival plot of FLT3/ITD MOLM-13 tumor-bearing mice treated with quizartinib, SGN-CD123A or a combination.

FIG. 6 shows the survival rates of FLT3/ITD MOLM-13 tumor-bearing mice treated with different agents. A half million MOLM-13 cells were implanted with matrigel subcutaneously in SCID mice. Tumor growth was monitored throughout the course of the study with bilateral vernier caliper measurements, and mean tumor volumes were calculated using the equation (0.5×[length×width$^2$]). When tumors reached approximately 100 mm$^3$, this marked day 1 of dosing and mice were randomly assigned into groups of 8 mice to receive quizartinib, SGN-CD123A, or quizartinib in combination with quizartinib.

As shown in FIG. 6, the survival plot of FLT3/ITD MOLM-13 tumor-bearing mice used tumor volume quadrupling time as readout. In this assay, 2 mg/kg quizartinib was given daily for 21 days, while 25 mcg/kg of SGN-CD123A was given once by intraperitoneal injection. The median survival time for animals in the untreated, quizartinib, SGN-CD123A, and the combination groups (SGN-CD123A and quizartinib) was 13 days, 24 days, 36 days, and >74 days (not reached), respectively (n=6, p<0.017 using log rank test). Mice with advanced tumor burden were sacrificed upon reaching tumor volumes of greater than 400 mm$^3$ or showing symptoms of hind limb paralysis, cranial swelling, and/or moribundity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cancer comprising a FLT3 mutation in a subject in need of such treatment, the method comprising the step of administering an antibody drug conjugate (ADC) and an FLT3 inhibitor, wherein the ADC comprises a PBD cytotoxic agent and an antibody, wherein the FLT-3 inhibitor is quizartinib, and wherein the antibody is: 1) h2H12 that specifically binds to a human CD33 protein; or 2) h7G3 that specifically binds to a human CD123 protein.

2. The method of claim 1, wherein the PBD cytotoxic agent has the formula

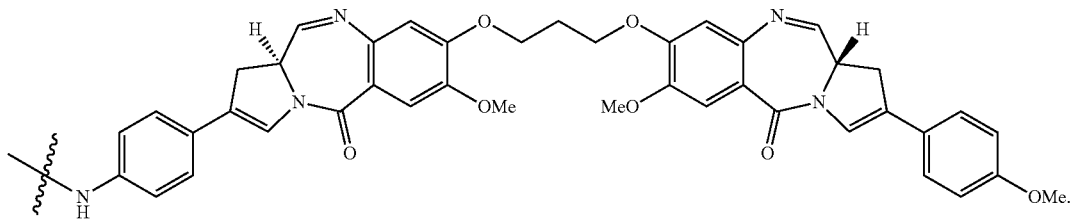 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

3. The method of claim 2, wherein the antibody is h2H12 that specifically binds to a human CD33 protein.

4. The method of claim 2, wherein the antibody is h7G3 that specifically binds to a human CD123 protein.

5. A method of treating cancer in a subject in need of such treatment, the method comprising the step of administering an antibody drug conjugate (ADC) and an FLT3 inhibitor, wherein the ADC comprises a PBD cytotoxic agent and an antibody, wherein the FLT3 inhibitor is quizartinib, wherein the cancer cell has a FLT3 mutation that results in decreased FLT3 expression or function as compared to a reference cell from the subject that does not have the FLT3 mutation, and wherein the antibody is: 1) h2H12 that specifically binds to a human CD33 protein; or 2) h7G3 that specifically binds to a human CD123 protein.

6. The method of claim 5, wherein the PBD cytotoxic agent has the formula

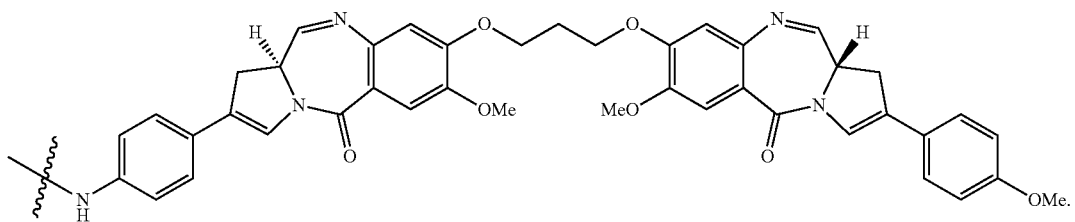 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]
7. The method of claim 5, wherein the antibody h2H12 that specifically binds to a human CD33 protein.
8. The method of claim 5, wherein the antibody is h7G3 that specifically binds to a human CD123 protein.
* * * * *

SEQUENCE LISTING

<160> NUMBER OF SEQ ID NOS: 15

<210> SEQ ID NO 1
<211> LENGTH: 107
<212> TYPE: PRT
<213> ORGANISM: Artificial Sequence
<220> FEATURE:
<223> OTHER INFORMATION: 2H12 LG  Light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu Ile Lys
            100                 105

<210> SEQ ID NO 2
<211> LENGTH: 117
<212> TYPE: PRT
<213> ORGANISM: Artificial Sequence
<220> FEATURE:
<223> OTHER INFORMATION: 2H12 HI  Heavy chain variable region

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
        115

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5                   10                  15

```
Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 5
<211> LENGTH: 329
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 6
<211> LENGTH: 330
<212> TYPE: PRT
<213> ORGANISM: Homo sapiens

<400> SEQUENCE: 6

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 7
<211> LENGTH: 329
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 8
<211> LENGTH: 120
<212> TYPE: PRT
<213> ORGANISM: Artificial Sequence
<220> FEATURE:
<223> OTHER INFORMATION: Heavy chain variable region for h7G3
```

<400> SEQUENCE: 8

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 9
<211> LENGTH: 114
<212> TYPE: PRT
<213> ORGANISM: Artificial Sequence
<220> FEATURE:
<223> OTHER INFORMATION: Light chain variable region for h7G3

<400> SEQUENCE: 9

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg

<210> SEQ ID NO 10
<211> LENGTH: 107
<212> TYPE: PRT
<213> ORGANISM: Artificial Sequence
<220> FEATURE:
<223> OTHER INFORMATION: hBU12 Light chain variable region

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
            50                  55                  60

Gly Ser Gly Thr Asp Phe Thr Leu Thr Ile Ser Ser Leu Glu Pro Glu
 65                  70                  75                  80

Asp Val Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 11
<211> LENGTH: 120
<212> TYPE: PRT
<213> ORGANISM: Artificial Sequence
<220> FEATURE:
<223> OTHER INFORMATION: hBU12 Heavy chain variable region

<400> SEQUENCE: 11

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Thr Ser
             20                  25                  30

Gly Met Gly Val Gly Trp Ile Arg Gln His Pro Gly Lys Gly Leu Glu
         35                  40                  45

Trp Ile Gly His Ile Trp Trp Asp Asp Lys Arg Tyr Asn Pro Ala
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
            115                 120

<210> SEQ ID NO 12
<211> LENGTH: 298
<212> TYPE: PRT
<213> ORGANISM: Artificial Sequence
<220> FEATURE:
<223> OTHER INFORMATION: H1F6 light chain variable region

<400> SEQUENCE: 12

Ala Ser Pro Ile Leu Glu Val Ala Leu Met Glu Thr Thr His Arg Gly
 1               5                  10                  15

Leu Asn Ser Glu Arg Pro Ala Ser Pro Ser Glu Arg Leu Ala Leu Ala
             20                  25                  30

Val Ala Leu Ser Glu Arg Leu Gly Leu Tyr Glu Ala Arg Gly Ala Leu
         35                  40                  45

Ala Thr His Arg Ile Leu Glu Ala Ser Asn Cys Tyr Ser Ala Arg Gly
         50                  55                  60

Ala Leu Ala Ser Glu Arg Leu Tyr Ser Ser Glu Arg Val Ala Leu Ser
 65                  70                  75                  80

Glu Arg Thr His Arg Ser Glu Arg Gly Leu Tyr Thr Tyr Arg Ser Glu
                 85                  90                  95

Arg Pro His Glu Met Glu Thr His Ile Ser Thr Arg Pro Thr Tyr Arg
            100                 105                 110

Gly Leu Asn Gly Leu Asn Leu Tyr Ser Pro Gly Leu Tyr Gly Leu Asn
            115                 120                 125

Pro Pro Leu Tyr Ser Leu Leu Ile Leu Glu Thr Tyr Arg Leu Ala Leu
            130                 135                 140

Ala Ser Glu Arg Ala Ser Asn Leu Glu Ser Glu Arg Gly Leu Tyr Val
145                 150                 155                 160

Ala Leu Pro Ala Ser Pro Ala Arg Gly Pro His Glu Ser Glu Arg Gly
                165                 170                 175

Leu Tyr Ser Glu Arg Gly Leu Tyr Ser Glu Arg Gly Leu Tyr Thr His
            180                 185                 190

Arg Ala Ser Pro Pro His Glu Thr His Arg Leu Thr His Arg Ile Leu
        195                 200                 205

Glu Ser Glu Arg Ser Glu Arg Leu Gly Leu Asn Ala Leu Ala Glu Ala
210                 215                 220

Ser Pro Val Ala Leu Ala Leu Ala Val Ala Leu Thr Tyr Arg Thr Tyr
225                 230                 235                 240

Arg Cys Tyr Ser Gly Leu Asn His Ile Ser Ser Glu Arg Ala Arg Gly
                245                 250                 255

Glu Val Ala Leu Pro Thr Arg Pro Thr His Arg Pro His Glu Gly Leu
            260                 265                 270

Tyr Gly Leu Asn Gly Leu Tyr Thr His Arg Leu Tyr Ser Val Ala Leu
            275                 280                 285

Glu Ile Leu Glu Leu Tyr Ser Ala Arg Gly
290                 295

<210> SEQ ID NO 13
<211> LENGTH: 334
<212> TYPE: PRT
<213> ORGANISM: Artificial Sequence
<220> FEATURE:
<223> OTHER INFORMATION: H1F6 heavy chain variable region

<400> SEQUENCE: 13

Gly Leu Asn Val Ala Leu Gly Leu Asn Leu Val Ala Leu Gly Leu Asn
1               5                   10                  15

Ser Glu Arg Gly Leu Tyr Ala Leu Ala Glu Val Ala Leu Leu Tyr Ser
            20                  25                  30

Leu Tyr Ser Pro Gly Leu Tyr Ala Leu Ala Ser Glu Arg Val Ala Leu
        35                  40                  45

Leu Tyr Ser Val Ala Leu Ser Glu Arg Cys Tyr Ser Leu Tyr Ser Ala
    50                  55                  60

Leu Ala Ser Glu Arg Gly Leu Tyr Thr Tyr Arg Thr His Arg Pro His
65                  70                  75                  80

Glu Thr His Arg Ala Ser Asn Thr Tyr Arg Gly Leu Tyr Met Glu Thr
                85                  90                  95

Ala Ser Asn Thr Arg Pro Val Ala Leu Ala Arg Gly Leu Asn Ala
            100                 105                 110

Leu Ala Pro Gly Leu Tyr Gly Leu Asn Gly Leu Tyr Leu Leu Tyr Ser
        115                 120                 125

Thr Arg Pro Met Glu Thr Gly Leu Tyr Thr Arg Pro Ile Leu Glu Ala
    130                 135                 140

Ser Asn Thr His Arg Thr Tyr Arg Thr His Arg Gly Leu Tyr Glu Pro
145                 150                 155                 160

Thr His Arg Thr Tyr Arg Ala Leu Ala Ala Ser Pro Ala Leu Ala Pro
                165                 170                 175

His Glu Leu Tyr Ser Gly Leu Tyr Ala Arg Gly Val Ala Leu Thr His
            180                 185                 190

Arg Met Glu Thr Thr His Arg Ala Arg Gly Ala Ser Pro Thr His Arg
        195                 200                 205

Ser Glu Arg Ile Leu Glu Ser Glu Arg Thr His Arg Ala Leu Ala Thr
        210                 215                 220

Tyr Arg Met Glu Thr Glu Leu Ser Glu Arg Ala Arg Gly Leu Ala Arg
225                 230                 235                 240

Gly Ser Glu Arg Ala Ser Pro Ala Ser Pro Thr His Arg Ala Leu Ala
                245                 250                 255

Val Ala Leu Thr Tyr Arg Thr Tyr Arg Cys Tyr Ser Ala Leu Ala Ala
                260                 265                 270

Arg Gly Ala Ser Pro Thr Tyr Arg Gly Leu Tyr Ala Ser Pro Thr Tyr
        275                 280                 285

Arg Gly Leu Tyr Met Glu Thr Ala Ser Pro Thr Tyr Arg Thr Arg Pro
        290                 295                 300

Gly Leu Tyr Gly Leu Asn Gly Leu Tyr Thr His Arg Thr His Arg Val
305                 310                 315                 320

Ala Leu Thr His Arg Val Ala Leu Ser Glu Arg Ser Glu Arg
                325                 330

<210> SEQ ID NO 14
<211> LENGTH: 107
<212> TYPE: PRT
<213> ORGANISM: Artificial Sequence
<220> FEATURE:
<223> OTHER INFORMATION: Mature light chain variable region of humanized
      20F3 LD

<400> SEQUENCE: 14

Gln Ile Val Leu Ser Gln Ser Pro Ala Thr Leu Ser Leu Ser Pro Gly
1               5                   10                  15

Glu Arg Ala Thr Met Ser Cys Arg Ala Ser Ser Ser Val Ser His Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95

Phe Gly Gly Gly Thr Lys Val Glu Ile Lys Arg
            100                 105

<210> SEQ ID NO 15
<211> LENGTH: 118
<212> TYPE: PRT
<213> ORGANISM: Artificial Sequence
<220> FEATURE:
<223> OTHER INFORMATION: Mature heavy chain variable region of humanized
      20F3 HD

<400> SEQUENCE: 15

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

```
Gly Met Asn Trp Val Arg Gln Ala Pro Gly Gln Asp Leu Lys Trp Met
        35                  40                  45
Gly Trp Ile Asn Thr Tyr Ser Gly Glu Pro Arg Tyr Ala Asp Asp Phe
    50              55                  60
Lys Gly Arg Phe Val Phe Ser Leu Asp Lys Ser Val Asn Thr Ala Tyr
65              70                  75                      80
Leu Gln Ile Ser Ser Leu Lys Ala Glu Asp Thr Ala Val Tyr Tyr Cys
            85                  90                      95
Ala Arg Asp Tyr Gly Arg Trp Tyr Phe Asp Val Trp Gly Gln Gly Thr
            100                 105                 110
Thr Val Thr Val Ser Ser
        115
```